US008124052B2

(12) United States Patent
Wellstein et al.

(10) Patent No.: US 8,124,052 B2
(45) Date of Patent: Feb. 28, 2012

(54) METHOD FOR IDENTIFYING TARGETING DOMAINS AND METHODS AND COMPOSITIONS COMPRISING THE SAME

(75) Inventors: Anton Wellstein, Washington, DC (US); Kevin J. McDonnell, Little Neck, NY (US); Justinian R. Ngaiza, Salisbury, MD (US)

(73) Assignee: Georgetown University, Washington, DC (US)

(*) Notice: Subject to any disclaimer, the term of this patent is extended or adjusted under 35 U.S.C. 154(b) by 985 days.

(21) Appl. No.: 10/364,907

(22) Filed: Feb. 10, 2003

(65) Prior Publication Data

US 2004/0170956 A1 Sep. 2, 2004

(51) Int. Cl.

| | |
|---|---|
| ***A61K 51/08*** | (2006.01) |
| ***A61K 38/17*** | (2006.01) |
| ***C12Q 1/70*** | (2006.01) |
| ***G01N 33/53*** | (2006.01) |
| ***C07H 21/04*** | (2006.01) |
| ***C07K 14/00*** | (2006.01) |

(52) U.S. Cl. ............ 424/1.69; 435/5; 435/7.8; 530/324; 530/350; 536/23.5

(58) Field of Classification Search ........................ None
See application file for complete search history.

(56) References Cited

U.S. PATENT DOCUMENTS

| | | | | |
|---|---|---|---|---|
| 5,622,699 | A | 4/1997 | Ruoslahti et al. | |
| 6,068,829 | A | 5/2000 | Ruoslahti et al. | |
| 6,174,687 | B1 | 1/2001 | Rajotte et al. | |
| 6,180,084 | B1 | 1/2001 | Ruoslahti et al. | |
| 6,232,287 | B1 | 5/2001 | Ruoslahti et al. | |
| 6,245,898 | B1 * | 6/2001 | Testa et al. | 530/388.85 |
| 6,296,832 | B1 | 10/2001 | Ruoslahti et al. | |
| 6,303,573 | B1 | 10/2001 | Ruoslahti et al. | |
| 6,306,365 | B1 | 10/2001 | Ruoslahti et al. | |
| 6,399,575 | B1 | 6/2002 | Smith et al. | |
| 6,491,894 | B1 | 12/2002 | Ruoslahti et al. | |
| 6,528,481 | B1 | 3/2003 | Burg et al. | |
| 6,576,239 | B1 | 6/2003 | Ruoslahti et al. | |
| 6,610,651 | B1 | 8/2003 | Ruoslahti et al. | |
| 6,613,517 | B2 * | 9/2003 | Michelotti | 435/6 |
| 6,743,892 | B1 | 6/2004 | Ruoslahti et al. | |
| 2001/0046498 | A1 | 11/2001 | Ruoslahti et al. | |
| 2003/0045476 | A1 | 3/2003 | Ruoslahti et al. | |
| 2003/0113320 | A1 | 6/2003 | Ruoslahti et al. | |
| 2003/0152578 | A1 | 8/2003 | Ruoslahti et al. | |
| 2003/0232762 | A1 | 12/2003 | Ruoslahti et al. | |
| 2004/0071689 | A1 | 4/2004 | Ruoslahti et al. | |
| 2004/0087499 | A1 | 5/2004 | Laakkonen et al. | |
| 2004/0096441 | A9 | 5/2004 | Ruoslahti et al. | |
| 2006/0239968 | A1 * | 10/2006 | Arap et al. | 424/93.2 |
| 2008/0193510 | A1 | 8/2008 | Wu et al. | |
| 2010/0119444 | A1 | 5/2010 | Wu et al. | |

FOREIGN PATENT DOCUMENTS

| | | | |
|---|---|---|---|
| WO | WO 02/068579 | * | 9/2002 |
| WO | WO03/066639 | A2 | 8/2003 |
| WO | WO 2010/053763 | A1 | 5/2010 |

OTHER PUBLICATIONS

Rajotte et al (Journal of Clinical Investigation, 1998, vol. 102, pp. 430-437).*
Haas et al (PNAS, 1988, vol. 85, pp. 2250-2254).*
NLM Gateway Mesh Term Information for GRP78 (downloaded from the Web, Jun. 19, 2009).*
Grimm et al (Journal of Immunological Methods, 1995, vol. 186, pp. 305-312).*
Rosenberg et al (InNovations, (Newsletter of Novagen, Inc.), 1996, pp. 1-6).*
American Association for Cancer Research (PA28-alpha Subunit: A Liver Homing Protein Identified from a Colon Cancer Cell Line by in Vivo Phage Display) vol. 42, Mar. 2001.
Stoica, Gerald E., et al., "Identification of Anaplastic Lymphoma Kinase as a Receptor for the Growth Factor Pleiotrophin," *The Journal of Biological Chemistry*, 276(20):16772-16779 (2001).
Azzazy, Hassan M.E., et al., "Phage Display Technology: Clinical Applications and Recent Innovations," *Clinical Biochemistry*, 35:425-445 (2002).
An, Ping, et al., "Suppression of Tumor Growth and Metastasis by a Vegfr-1 Antagonizing Peptide Identified from a Phage Display Library," *Int. J. Cancer*, 111(2):165-173 (2004).
Hetian, Lei, et al., "A Novel Peptide Isolated from a Phage Display Library Inhibits Tumor Growth and Metastasis by Blocking the Binding of Vascular Endothelial Growth Factor to its Kinase Domain Receptor," *The Journal of Biological Chemistry*, 277(45):43137-43142 (2002).
GenCore Accession No. BE874057, Oct. 2000.
GenCore Accession No. BG402877, Mar. 2001.
GenCore Accession No. AZ537350, Nov. 2000.
GenCore Accession No. AA463349, Jun. 1997.
GenCore Accession No. BG391890, Mar. 2001.
GenCore Accession No. AI961628, Mar. 2000.
GenCore Accession No. AW794218, May 2000.
GenCore Accession No. X85671, Jul. 1995.
GenCore Accession No. BI825856, Oct. 2001.
Chang et al. "Antiangiogenic Targeting Liposomes Increase Therapeutic Efficacy for Solid Tumors" *Journal of Biological Chemistry* May 2009 284(19): 12905-12916.

* cited by examiner

*Primary Examiner* — Karen Canella
(74) *Attorney, Agent, or Firm* — Wolf, Greenfield & Sacks, P.C.

(57) ABSTRACT

The present invention is directed to a method of identifying tissue targeting domains. In particular, the invention relates to methods for identifying a polynucleotide encoding a targeting domain which directs tumor cell localization to secondary sites, to methods of utilizing the polynucleotide and corresponding polypeptide or fragments thereof and compositions comprising the same.

35 Claims, 17 Drawing Sheets

Liver enrichment and organ distribution of LS174T Phage after *in vivo* selection

LS174T Clones isolated after 4 rounds of selection

| Clone ID | frequency (%) of clones | peptide length of insert |
|---|---|---|
| LS42 | 17 (28.3) | 151 |
| JN40 | 6 (10) | 156 |
| SW50 | 4 (6.7) | 30 |
| JN42 | 4 (6.7) | 21 |
| LS45 | 3 (5) | 211 |
| LS48 | 3 (5) | 46 |
| SW59 | 3 (5) | 27 |
| SW48 | 2 (3.2) | 181 |
| SW58 | 2 (3.2) | 181 |

GAATTCAAGCAAAGTATTTATCTNGACTCGCCACACTCCACGGGAAAGCAATATGAAATGA
TCTGCTGCAGTGCTCTGAGCCCTAGGATTCATCTTTCTTTTCACCGTAGGTGGCCTGACTG
GCATTGTATTAGCAAACTCATCACTAGACATCGTACTACACGACACGTACTACGTTGTAGC
TCACTTCCACTATGTCCTATCAATAGGAGCTGTATTTGCCATCATAGGAGGCTTCATTCAT
TGATTTCCCCTATTCTCAGGCTACACCCTAGACCAAACCTACGCCAAAATCCATTTCACTA
TCATATTCATCGGCGTAAATCTAACTTTCTTCCCACAACACTTTCTCGGCCTAACCGGAAT
GCCCCGACGTTACTCGGACTACCCCGATGCATACACCACATGAAACATCCTATCATCTGTA
GGCTCAAGCTTGCGGCCGCACTCGAGTAACTAGTTTACCCCTTGGGGCCTCTAAACGGGTC
TTGAGGGGT (SEQ ID NO 1)

SW50

GAATTCAAGCGCACCTTTCAGAAGCTACACTAGCAGGAAAAAATTCCATCAAGCAATTNCA
TTAGTAATTTNCNATAATTNCACAAAAGATNCTTGATCTTACTTGAAGTATACATGAGGGG
AAAGAGCCCCCTCAGCAGGTGTTCCCGTTGCTTACAGAAGCAAACTAAAGGACCTAAAACT
GGAGGCAAGCCAGGATGCCAAAAAGGGGGAAGAGAAATGATAAAGAACCATTCATAAATTC
CATGTCTACTTCAAGACATTTGTCTAATGACCCTTACATAATAAGTATTTTAGGGAAAACT
ACCACCCTTTTAAGATAAAAGTACAATCTTAAAAGCTGTAGTTCTCAATTATAGTAATATT
TCTTACTTCCAGTAATATGTCTCAATACCTTGGACTGCTGGATGTCAAAAGACAATACCTG
GGGGTCATCTNTGAGATCTGAACAAATAGAGGAATTCTCTAGGACTGTATACTCTCTATTT
TGGCTTTTTGAATGAAGTACAGACAGGCTTCTCTGCTATCCTCCAGGCAGTGTAATAGTCA
AGGAAAAGGGCAACAGTTTTGGATCATTCCTTAGACACTAATCAGCTGGGGAAAGAGTTCA
TTGGNAAAAGTGTCCTCCCAAGAATGGTTTACACCAAGCAGAGAGGACATGTCACTGAAAT
GGGGAAAGGGAAACCCCCGTTTCCACAGTCACTGTTAGCA (SEQ ID NO 2)

SW58

GAATTCANGCGAAGGATATGCANAAGNGATGTCCACAAGAGTTCATTGANCGCTGAAATGA
AACTCTTTGCTCAACAATGCAAGGAGGTACNACATCCTTATCATCACAGCACTTATTCCAG
GTAAAAAANCTCCANTTTTATTTAATANNNNAATGANTGNGTCACTGAAGGAAGGTTCAGT
TGTTNNNNCTTTACCTGCNGANGCNGGCGNAAACNTTGATANCNCCTTGGGGCGACAANNC
NGGTNTCAGAGGGGNAATTACTCACATCGGCGAGAGGNGAGCTGGCCACGGGGGGGGNCAC
TCAGGCCNGCACCCTNGATTCCAACNNCATCACCNNACNNNTGAAGGCCATCANCCCNGAC
AAAGATACTTTTTATTTTGATGTGAAAGANGACTTTCNCNTTGGTACNATNGGTNNTTTCC
ATNTCGGNNCTNNNGNGNTNNAAGGTGGTAAAGGAANTTTTCCCCCNGNCNTNCNGGNNCC
CGTGNNCCCCACCGTCCNGNNCTTCGNCCGCCCCACTNCTNTNC (SEQ ID NO 3)

SW59

GAATTCAAGCANACTTTGGGGAAAAGGAGGTTCTTAAAATCAGTGTTTCCCCTTTGTGCAC
TTGTAGAAAAAAAAGAAANACCTTCTAGAGCTGATTTGATGGACAATGGANANAGCNNNCC
CTGTGNNTATNATAANGGAAGCTAGCTGCTCTNCGGTCACCTTTGCNTAGNANNATACTTT
AACCTGGCTTTTACAGNAGTAGTAACTGCCCTCCAACCGTCTTAANNGNNAATNTCGGAGC
CNATTGCGCNGTGNTCCACCTACGGCNAATATTTNCNCCNAGGAGGATGGNTTTCCCNGCC
AGTANTNCCTTNGCNTTNAACCTCACGTGACCTTCTTANGCNATTCNCGCTCGCCGCAAGA
NGTCTTTGTTNTTCCCTTCTCGCACTCCTTNTNTNTCTNNGNGCCGTGNCGNCCNCTTCCT
TNCGCTGACCNGGCTCGNNNCTNNTTGCNCNTTCAGGGNGCTCTTNCCAAGCTCCTCNGGG
NTNNTGCATTTTTTNCNCCCNGNNTGNCNGCCCCNCCGCCCNGCNCCTGNTTCAGCCTTAC
ACTTCNGGCANCGGCCTACANGGGGATAAANCANNCATTTGTCNCGGGCGTTTACNTNCTC
CCGTCCCACCATCTNNGCCATNTTCNCCNNGGGNNGTNCTTTTNCTACCTCCCCCCCCCNC
NCNCTNCANTCNTTTACCNGTTCGCGCTCCTCTNTGCGTTCGNGCCNCCNCGTCGCNCTTT
TNCNNCNCTTT (SEQ ID NO 4)

GAATTCAAGCGGAACGCTCACGGACTGTGTGGTAATGAGAGATCCAAACACCAAGCGCTCC
AGGGGCTTTGGGTTTGTCACATATGCCACTGTGGAGGAGGTGGATGCAGCTATGAATGCAA
GGCCACACAAGGTGGATGGAAGAGTTGTGGAACCAAAGAGAGCTGTCTCCAGAGAAGATTC
TCAAAGACCAGGTGCCCACTTAACTGTGAAAAAGATATTTGTTGGTGGCATTAAAGAAGAC
ACTGAAGAACATCACCTAAGAGATTATTTTGAACAGTATGGAAAAATTGAAGTGATTGAAA
TCATGACTGACCGAGGCAGTGGCAAGAAAAGGGGCTTTGCCTTTGTAACCTTTGACGACCA
TGACTCCGTGGATAAGATTGTCATTCAGAAATACCATACTGTGAATGGCCACAACTGTGAA
GTTAGAAAAGCCCTGTCAAAGCAAGAGATGGCTAGTGCTTCATCCAACCAAAGAGGTCGAA
GTGGTTCTGGAAACTTTGGTGGTGGTCGTGGAGGTGGTTTCAGTGGGAATGACAACTTCNG
TCCTGGAGGAAACTTNNANTGGTCCTGGTGGCTTTGGTGGCAACCGTGGTGGTGGTGGATA
TGGTGGCAATGGGGATGGCTATAATGGATTTGGTATGATGGAANCAATTTTGGNGGTGGTG
GAAGCTACANTGATTTTGGGAANTAAAACAATCAATCCTCAAA (SEQ ID NO 5)

JN42

AAATTCANGCGTTATCGTCCTTTCTTCCATTCTTAACAGTATGTGCCCATTTGCAAAACAA
AAATGCTAATAATCAGTAATAGTCCTATAAAAGATGTTAACTCTGTTTAGTCATTGACTGA
TCTTGCTCTAACCTTAAAATTTTGTGATTATTGACCTCTGTTGCATTTATTCTAAAGCCCC
CCGAAGCTTGCGGCCGCACTCGAGTAACTAGTTAACCCCTTGGGGCCTCTAAACGGGTCTT
GAGGGGTAACTTGGNTCCTCGNGGGNGGNGGCANGCTTCGGGGGGGTTTG (SEQ ID NO
6)

LS42

GAATTCAAGCAAGACAAGGATGAAAAGAAGAAGGGGGAGGATGAAGACAAAGGTCCTCCCT
GTGGCCCAGTGAACTGCAATGAAAAGATCGTGGTCCTTCTGCAGCGCTTGAAGCCTGAGAT
CAAGGATGTCATTGAGCAGCTCAACCTGGTCACCACCTGGTTGCAGCTGCAGATACCTCGG
ATTGAGGATGGTAACAATTTTGGAGTGGCTGTCCAGGAGAAGGTGTTTGAGCTGATGACCA
GCCTCCACACCAAGCTAGAAGGCTTCCACACTCAAATCTCTAAGTATTTCTCTGAGCGTGG
TGATGCAGTGACTAAAGCAGCCAAGCAGCCCCATGTGGGTGATTATCGGCAGCTGGTGCAC
GAGCTGGATGAGGCAGAGTACCGGGACATCCGGCTGATGGTCATGGAGATCCGCAATGCTT
ATGCTGTGTTATATGACATCATCCTGAAGAACTTCGAGAAGCTCAAGAAGCCCAGGGGAGA
AACAAAGGGAATGATCTATTGAGAGCCCTCTCTCCCATTCTGTGATGAGTACAGCAGANAC
CTTCCTGCTTTTTANTGGGGACCCANATTTTCCCCAAACTTGCTCTGTTGAGATTTTTCCC
TCACCTTGCCTCTCANGCACAATAAATATANTTATACCACTGCCAAAGCTTGCGGGCGCAC
TCCANTAACTAGTTAACCCCTTGGGGCCTCTAAA
(SEQ ID NO 7)

LS45

GAATTCTCAAAATAGTTCAGAAAAATCATGTTTCAAAGTACTCACATTCTTCCAGATGAGG
AAAAAATGGTGAAGGAAAGAAAAAGGAAATTGAAAGAAGTATTAATCCAAACTTTCAAAGA
AAATCAACAGTGTCAAAAACGGTATTTCGCTGCCTGGCACAAGCTGATTCTTGATCATAGG
ATTAAGCTGGGGAAAGCTGGGACCCTGTCTGACTGGAAGATTCAGCTGAAGGTCCTGCGGG
CCTGGAGAGACTACACAAGATTCCAGAAGTTGGAGCGGGAGACTCAAGCCTTGGAAAATGA
TCTTAGGGAAGAAAACAGAAAACAACAACTGGCCACTGAGTATAACCGGAAACAAGTTCTC
CGACACTGCTTTACAGAATGGCAGCATTGGCATGGCGCCGAGCTCCTGAAGAGAGAGCTGG
CTCTCACAAAAGAGGAAACTANGAAGAAGATGGNTGCACTGCTGCAGGCAGCATCACTGGG
GAAACTCAGTGCCANTGGGTTATCANGCNTCAGTCNACCTGAGGANGGAACAGCCNTGGTG
GGTNCNCCANTNAANAATGGNCAGGANACNGCNNTGCCCCCNTTTGTGGGAAAAGCCCCCC
TTGGGNAGCANTGGGTGNNTNTCNNTCCCCCCCNGGGAAGNACAANA (SEQ ID NO 8)

FIGURE 6B

LS48
GAATTCTGGAAAGTTGGGTACAACTGTGAAGCCAAAGAGTCTGGTTACTTCAAGTTCTGGG
GCTTTAAAAAAGCAGCATAAGAAGCCCTTTGATGCAATGAATAACATTGTGGCAAATTTGC
TCCTCAACCTAACGAGGGAAGCTTGCGGCCGCACTCGAGTAACTAGTTAACCCCTTGGGGC
CTCTAAACGGGTCTTGAGGGGTNTACTAAGTTACTCGAGTGCGGCCGCAAGCTTCCCTCGT
TAGGTTGAGGAGCAAATTTGCCACAATGTTATTCATTGCATCAAAGGGCTTCTTATGCTGC
TTTTTTAAAGCCCCAGAACTTGAAGTAACCAGACTCTTTGGCTTCACAGTTGTACCCAACT
TTCCAGAATTCGGATCCCCGAGCATCACACCTGACTGGAATACGACAGCTNCAA
(SEQ ID NO 9)

FIGURE 6C

SW48
Frame 1
X N S S K V F I X T R H T P R E S N M K S A A V L A L G F I F
L F T V G G L T G I V L A N S S L D I V L H D T Y Y V V A H F
H Y V L S I G A V F A I I G G F I H F P L F S G Y T L D Q T Y
A K I H F T I I F I G V N L T F F P Q H F L G L T G M P R R Y
S D Y P D A Y T T N I L S S V G S S L R P H S S N F T P W G L
T G L E G (SEQ ID NO 10)

Frame 2
X I Q A K Y L S X L A T L H G K A I N D L L Q C S E P D S S F
F S P V A L A L Y Q T H H T S Y Y T T R T T L L T S T M S Y
Q E L Y L P S E A S F I D F P Y S Q A T P T K P T P K S I S L
S Y S S A I L S S H N T F S A P E C P D V T R T T P M H T P H
E T S Y H L A Q A C G R T R V T S L P L G A S K R V L R G
(SEQ ID NO 11)

Frame 3
E F K Q S I Y X D S P H S T G K Q Y E M I C C S A L S P R I H
L S F H R R W P D W H C I S K L I T R H R T T R H V L R C S S
L P L C P I N R S C I C H H R R L H S L I S P I L R L H P R P
N L R Q N P F H Y H I H R R K S N F L P T T L S R P N R N A P
T L L G L P R C I H H M K H P I I C R L K L A A A L E LVY P L
G P L N G S G (SEQ ID NO 12)

SW50
Frame 1
X N S S A P F R S Y T S R K K F H Q A I X L V I X X N X T K D
X S Y L K Y T G E R A P S A G V P V A Y R S K L K D L K L E A
S Q D A K K G E E K R T I H K F H V Y F K T F V P L H N K Y F
R E N Y H P F K I K V Q S K L F S I I V I F L T S S N M S Q Y
L G L L D V K R Q Y L G V I X E I T N R G I L D C I L S I L A
F M K Y R Q A S L L S S R Q C N S Q G K G Q Q F W I I P T L I
S W G K S S L X K V S S Q E W F T P S R E D M S L K W G K G N
P R F H S H C (SEQ ID NO 13)

Frame 2
X I Q A H L S E A T L A G K N S I K Q X H F X I I X Q K X L D
L T S I H E G K E P P Q Q V F P L L T E A N R T N W R Q A R M
P K R G K R N D K E P F I N S M S T S R H L S N D P Y I I S I
L G K T T T L L R K Y N L K S C S S Q L Y F L L P V I C L N T
L D C W M S K D N T W G S S X R S E Q I E E F S R T V Y S L F
W L F E S T D R L L C Y P P G S V I V K E K G N S F G S F L R
H S A G E R V H W X K C P P K N G L H Q A E R T C H N G E R E
T P V S T V T V S (SEQ ID NO 14)

FIGURE 7A

Frame 3
E F K R T F Q K L H Q E K I P S S N X I S N X X X H K R X L I
L L E V Y M R G K S P L S R C S R C L Q K Q T K G P K T G G K
P G C Q K G G R E M I K N H S I P C L L Q D I C L M T L T V F
G K L P P F D K S T I L K A V V L N Y S N I S Y F Q Y V S I P
W T A G C Q K T I P G G H X D L N K R N S L G L Y T L Y F G F
L N E V Q T G F S A I L Q A V S R K R A T V L D H S L D T N Q
L G K E F I X K S V L P R M V Y T K Q R G H V T E M G K G K P
P F P Q S L L A (SEQ ID NO 15)

SW58
Frame 1
X N S X E G Y A X X M S T R V H X L K N S L L N N A R R Y X I
L I I T A L I P G K K X P X L F N X X M X X S L K E G S V V X
X L P X X X G X N X D X X L G R Q X X X Q R X N Y S H R R E X
S W P R G G X L R X A P X I P X X S X X X R P S X X T K I L F
I L M K X T F X L V X X X X S X S X X X X X K V V K E X F P X
X X X X P X X P P S X X S X A P X X X
(SEQ ID NO 16)

Frame 2
X I X A K D M X K X C P Q E F I X R N E T L C S T M Q G G X T
S L S S Q H L F Q V K X L X F Y L I X X X X H R K V Q L X X L
Y L X X X A X X L I X P W G D X X G X R G X I T H I G E R X A
G H G G X H S G X H P X F Q X H H X X X E G H X P X Q R Y F L
F C E R X L X X W Y X X X F P X R X X X X X R W R X F S P X X
X X X R X P H R X X L X P P H X X X
(SEQ ID NO 17)

Frame 3
E F X R R I C X X D V H K S S L X A E M K L F A Q Q C K E V X
H P Y H H S T Y S R K X S X F I X X N X X V T E G R F S C X X
F T C X X X X K X X X L G A T X X X S E G X L L T S A R X E L
A T G G X T Q A X T X D S N X I T X X X K A I X X D K D T F Y
F D V K X D F X X G X X G X F H X X X X X X X X G G K G X F P X
X X X X P V X P T V X X F X R P T X X (SEQ ID NO 18)

SW59
Frame 1
X N S S X L W G K G G S N Q C F P F V H L K K K K X L L E L I
W T M X X X X P V X X I X E A S C S X V T F X X X T L T W L L
Q X L P S N R L X X X X R S X L R X X P P T X N I X X X E D X
F P X Q X X L X X X P H V T F L X X X R S P Q X V F V X P F S
H S X X X X X P X X X L P X A D X A X X X L X X Q X A L X K L
L X X X A F F X P X X X A X P P X X X F S L T L X A X A Y X G
I X X X F V X G V Y X L P S H H X X H X X X G X X F X Y L P P
X X X X X X Y X F A L L X A F X X X R R X F X X L
(SEQ ID NO 19)

FIGURE 7B

Frame 2
X I Q A X F G E K E V L K I S V S P L C T C R K K R X T F S F
D G Q W X X X X L X X X X K L A A X R S P L X X X I L P G F Y
X S S N C P P T V L X X N X G A X C X V X H L R X I F X X R R
M X F X A S X X X X X N L T P S X X I X A R R K X S L X F P S
R T P X X S X X R X X X F L X L T X L X X X C X F R X L X P S
S X G X X H F X X X X X X P X R X X P X S A L H F X X R P T X
G X X H L X R A F X X S R P T I X A X F X X X X X F X T S P P
X X X X X F T X S R S S X R S X X X V X L X X X F
(SEQ ID NO 20)

Frame 3
E F K X T L G K R R F L K S V F P L C A L V E K K E X P S R A
D L M D N G X S X P C X Y X X G S L L X G H L C X X X Y F N L
A F T X V V T A L Q P S X X X S E X I A X X S T Y G X Y X X X
G G W X S X P V X P X X X T S R D L L X X F X L A A R X L C X
S L L A L L X X X X A V X X X S X R X G S X X X X X S G X S X
Q A P X X X C I F X X X X X X P X A X X L X Q P Y T X G X G L
X G D K X X I C X G R L X X P V P P S X P X X X X X X L X L P
P P P X X X X X L X V R A P X C V X A X X S X F X X X
(SEQ ID NO 21)

JN40
Frame 1
X N S S G T L T D C V V M R D P N T K R S R G F G F V T Y A T
V E E V D A A M N A R P H K V D G R V V E P K R A V S R E D S
Q R P G A H L T V K K I F V G G I K E D T E E H H L R D Y F E
Q Y G K I E V I E I M T D R G S G K K R G F A F V T F D D H D
S V D K I V I Q K Y H T V N G H N C E V R K A L S K Q E M A S
A S S N Q R G R S G S G N F G G G R G G G F S G N D N F X P G
G N X X W S W W L W W Q P W W W W I W W Q W G W L W I W Y D G
X N F X G G G S Y X D F G X N N Q S S (SEQ ID NO 22)

Frame 2
X I Q A E R S R T V W E I Q T P S A P G A L G L S H M P L W R
R W M Q L M Q G H T R W M E E L W N Q R E L S P E K I L K D Q
V P T L K R Y L L V A L K K T L K N I T E I I L N S M E K L K
L K S L T E A V A R K G A L P L P L T T M T P W I R L S F R N
T I L M A T T V K L E K P C Q S K R W L V L H P T K E V E V V
L E T L V V V V E V V S V G M T T X V L E E T X X G P G G F G
G N R G G G G Y G G N G D G Y N G F G M M E X I L X V V E A T
X I L G X K T I N P Q (SEQ ID NO 23)

Frame 3
E F K R N A H G L C G N E R S K H Q A L Q G L W V C H I C H C
G G G G C S Y E C K A T Q G G W K S C G T K E S C L Q R R F S
K T R C P L N C E K D I C W W H R R H R T S P K R L F T V W K
N S D N H D P R Q W Q E K G L C L C N L R P L R G D C H S E I
P Y C E W P Q L S K S P V K A R D G C F I Q P K R S K W F W K
L W W W S W R W F Q W E Q L X S W R K L X X V L V A L V A T V
V V V D M V A M G M A I M D L V W X Q F W X W W K L X F W E X
K Q S I L K (SEQ ID NO 24)

FIGURE 7C

JN42
Frame 1
X N S X V I V L S S I L N S M C P F A K Q K C S V I V L K M L
T L F S H L I L L P N F V I I D L C C I Y S K A P R S L R P
H S S N LT P W G L T G L E G L X S S X X X A X F G G V
(SEQ ID NO 25)

Frame 2
X I X A L S S F L P F L T V C A H L Q N K N A N N Q S Y K R C
L C L V I D S C S N L K I L L L T S V A F I L K P P E A C G R
T R V T S P L G A S K R V L R G N L X P X G X X X A S G G F
(SEQ ID NO 26)

Frame 3
K F X R Y R P F F H S Q Y V P I C K T K M L I I S N S P I K D
V N S V S L T D L A L T L K F C D Y P L L H L F S P P K L A A
A L E L V N P L G P L N G S G V T W X L X X X G X L R G G L
(SEQ ID NO 27)

LS42
Frame 1
X N S S K T R M K R R R G R M K T K V L P V A Q T A M K R S W
S F C S A S L R S R M S L S S S T W S P P G C S C R Y L G L R
M V T I L E W L S R R R C L S P A S T P S K A S T L K S L S I
S L S V V M Q L K Q P S S P M W V I I G S W C T S W M R Q S T
G T S G W S W R S A M L M L C Y M T S S R T S R S S R S P G E
K Q R E S I E S P L S H S V M S T A X T F L L F X G D P X F P
Q T C S V E I F P S P C L S X T I N I X I P L P K L A G A L X
L V N P L G P L (SEQ ID NO 28)

Frame 2
X I Q A R Q G K E E G G G R Q R S S L W P S E L Q K D R G P S
A A L E A D Q G C H A A Q P G H H L V A A A D T S D G W Q F W
S G C P G E G V A D D Q P P H Q A R R L P H S N L V F L A W C
S D S S Q A A P C G L S A A G A R A G G R V P G H P A D G H G
D P Q C L C C V I H H P E E L R E A Q E A Q G R N K G N D L L
R A L S P I L V Q Q X P S C F L X G T X I F P K L A L L R F F
P H L A S X A Q I X L Y H C Q S L R A H S X N L T P W G L
(SEQ ID NO 29)

Frame 3
E F K Q D K D E K K K G E D E D K G P P C G P V N C N E K I V
V L L Q R L K P E I K D V I E Q L N L V T T W L Q L Q I P R I
E D G N N F G V A V Q E K V F E L M T S L H T KL E G F H T Q
I S K Y F S E R G D A V T K A A K Q P H V G D Y R Q L V H E L
D E A E Y R D I R L M V M E I R N A Y A V L Y D I I L K N F E
K L K K P R G E T K G M I Y E P S L P F C D E Y S R X L P A F
X W G P X F S P N L L C D F S L T L P L X H N K Y X Y T T A K
A C G R T P X T S P L G A S K (SEQ ID NO 30)

FIGURE 7D

LS45
Frame 1
X N S Q N S S E K S C F K V L T F F Q M R K K W R K E K G N K
K Y S K L S K K I N S V K N G I S L P G T S F L I I G L S W G
K L G P C L T G R F S R S C G P G E T T Q D S R S W S G R L K
P W K M I L G K K T E N N N W P L S I T G N K F S D T A L Q N
G S I G M A P S S R E S W L S Q K R K L X R R W X H C C R Q H
H W G N S V P X G Y X X S V X L R X E Q X W W X X X X X M X R
X X X C P X L W E K P P L X S X G X X X X P P X E X Q X
(SEQ ID NO 31)

Frame 2
X I L K I V Q K N H V S K Y S H S S R G K N G E G K K K E I E
R S I N P N F Q R K S T V S K T V F R C L A Q A D S S D A G E
S W D P V L E D S A E G P A G L E R L H K I P E V G A G D S S
L G K S G R K Q K T T T G H V P E T S S P T L L Y R M A A L A
W R R A P E E R A G S H K R G N X E E D X C T A A G S I T G E
T Q C X W V I X X Q X T G X N S X G G X X X X X W X G X X X A
P X C G K S P P W X A X G X X X S P X G K X X (SEQ ID NO 32)

Frame 3
E F S K F R K I M F Q S T H I L P D E E K M V K E R K R K L K
E V L I Q T F K E N Q Q C Q K R Y F A A W H K L I L D H R I K
L G K A G T L S D W K I Q L K V L R A W R D Y T R F Q K L E R
E T Q A L E N D L R E E N R K Q Q L A T E Y N R K Q V L R H C
F T E W Q H W H G A E L L K R E L A L T K E E T X K K M X A L
L Q A A S L G K L S A X G L S X X S X P E X G T A X V G X P X
X N X Q X X X X P X F V G K A P L G X X W V X X X P P X G X T
X (SEQ ID NO 33)

LS48
Frame 1
X N S G K L G T T V K P K S L V T S S S G A L K K Q H K K P F
D A M N N I V A N L L L N L T R E A C G R T R V T S P L G A S
K R V L R G X L S Y S S A A A S F P R V E E Q I C H N V I H C
I K G L L M L L F S P R T S N Q T L W L H S C T Q L S R I R I
P E H H T L E Y D S X (SEQ ID NO 34)

Frame 2
X I L E S W V Q L S Q R V W L L Q V L G L K S S I R S P L M Q
I T L W Q I C S S T R G K L A A A L E L V N P L G P L N G S G
X Y V T R V R P Q A S L V R L R S K F A T M L F I A S K G F L
C C F F K A P E L E V T R L F G F T V V P N F P E F G S P S I
T P D W N T T A X (SEQ ID NO 35)

Frame 3
E F W K V G Y N C E A K E S G Y F K F W G F K K A A E A L C N
E H C G K F A P Q P N E G S L R P H S S N L T P W G L T G L E
G X T K L L E C G R K L P S L G G A N L P Q C Y S L H Q R A S
Y A A F L K P Q N L K P D S L A S Q L Y P T F Q N S D P R A S
H L T G I R Q X Q (SEQ ID NO 36)

FIGURE 7E

Results of the statistical analysis. P-values for different settings.

Varying parameters between table-cells of one gene: Arrays included in the analysis
Significant p-values for the Fisher-exact-test are given in red.
(compare Figure 4 for details on how the analysis was performed).

| Gene | arrays used: COLON, primary AND metastasis | | | arrays used: COLON, primary ONLY | | |
|---|---|---|---|---|---|---|
| | Fisher | N Met+ | N Met- | Fisher | N Met+ | N Met- |
| LS42 | 0,000000816 | 31 | 21 | 0,005922845 | 10 | 21 |
| JN40 | < 0.00000001 | 31 | 21 | 0,000067708 | 10 | 21 |
| LS45 | 0,000682424 | 28 | 21 | 0,046384500 | 10 | 21 |
| SW48 | 0,001590599 | 29 | 21 | 0,046384500 | 10 | 21 |
| SW50 | 0,038199172 | 19 | 19 | 0,031677768 | 10 | 19 |

| Gene | arrays used: COLON, primary AND metastasis, PANCREAS-Adeno-Ca, AMPULLARY, BILE | | | arrays used: COLON, primary ONLY, PANCREAS Adeno-Ca, AMPULLARY, BILE | | |
|---|---|---|---|---|---|---|
| | Fisher | N Met+ | N Met- | Fisher | N Met+ | N Met- |
| PTN | 0,000330334 | 116 | 68 | 0,001685761 | 100 | 68 |
| FGF (ISH) | 0,251503683 | 116 | 68 | 0,070614954 | 100 | 68 |

Legend

| | |
|---|---|
| Fisher | p-value for Fisher-exact-test |
| N Met+ | "N" of metastasis positive |
| N Met- | "N" of metastasis negativ |

FIGURE 8

SEQUENCE LISTING

```
<160> NUMBER OF SEQ ID NOS: 36

<210> SEQ ID NO 1
<211> LENGTH: 497
<212> TYPE: DNA
<213> ORGANISM: Homo Sapien
<220> FEATURE:
<221> NAME/KEY: misc_feature
<222> LOCATION: 24
<223> OTHER INFORMATION: n = A,T,C or G
<220> FEATURE:
<221> NAME/KEY: misc_feature
<222> LOCATION: 24
<223> OTHER INFORMATION: n = A,T,C or G

<400> SEQUENCE: 1

gaattcaagc aaagtattta tctngactcg ccacactcca cgggaaagca atatgaaatg     60

atctgctgca gtgctctgag ccctaggatt catctttctt ttcaccgtag gtggcctgac    120

tggcattgta ttagcaaact catcactaga catcgtacta cacgacacgt actacgttgt    180

agctcacttc cactatgtcc tatcaatagg agctgtattt gccatcatag gaggcttcat    240
```

-continued

```
tcattgattt cccctattct caggctacac cctagaccaa acctacgcca aaatccattt    300

cactatcata ttcatcggcg taaatctaac tttcttccca caacactttc tcggcctaac    360

cggaatgccc cgacgttact cggactaccc cgatgcatac accacatgaa acatcctatc    420

atctgtaggc tcaagcttgc ggccgcactc gagtaactag tttacccctt ggggcctcta    480

aacgggtctt gaggggt                                                   497
```

```
<210> SEQ ID NO 2
<211> LENGTH: 711
<212> TYPE: DNA
<213> ORGANISM: Homo Sapien
<220> FEATURE:
<221> NAME/KEY: misc_feature
<222> LOCATION: 59, 72, 74, 81, 92, 438, 615
<223> OTHER INFORMATION: n = A,T,C or G
<220> FEATURE:
<221> NAME/KEY: misc_feature
<222> LOCATION: 59, 72, 74, 81, 92, 438, 615
<223> OTHER INFORMATION: n = A,T,C or G

<400> SEQUENCE: 2

gaattcaagc gcacctttca gaagctacac tagcaggaaa aaattccatc aagcaattnc     60

attagtaatt tncnataatt ncacaaaaga tncttgatct tacttgaagt atacatgagg    120

ggaaagagcc ccctcagcag gtgttcccgt tgcttacaga agcaaactaa aggacctaaa    180

actggaggca agccaggatg ccaaaaaggg ggaagagaaa tgataaagaa ccattcataa    240

attccatgtc tacttcaaga catttgtcta atgaccctta cataataagt attttaggga    300

aaactaccac ccttttaaga taaaagtaca atcttaaaag ctgtagttct caattatagt    360

aatatttctt acttccagta atatgtctca ataccttgga ctgctggatg tcaaaagaca    420

atacctgggg gtcatctntg agatctgaac aaatagagga attctctagg actgtatact    480

ctctattttg gctttttgaa tgaagtacag acaggcttct ctgctatcct ccaggcagtg    540

taatagtcaa ggaaaagggc aacagttttg gatcattcct tagacactaa tcagctgggg    600

aaagagttca ttggnaaaag tgtcctccca agaatggttt acaccaagca gagaggacat    660

gtcactgaaa tggggaaagg gaaacccccg tttccacagt cactgttagc a             711
```

```
<210> SEQ ID NO 3
<211> LENGTH: 532
<212> TYPE: DNA
<213> ORGANISM: Homo Sapien
<220> FEATURE:
<221> NAME/KEY: misc_feature
<222> LOCATION: 8, 23, 27, 50, 92, 131, 137, 150, 151, 152, 153, 159,
      162, 188, 189, 190, 191, 202, 205, 208, 213, 218, 225, 227, 242,
      243, 245, 249, 259, 282, 302, 313, 321, 331, 332, 340, 341,
      344, 345, 346, 359, 363, 396, 404, 406, 414, 417, 421
<223> OTHER INFORMATION: n = A,T,C or G
<220> FEATURE:
<221> NAME/KEY: misc_feature
<222> LOCATION: 422, 430, 435, 436, 439, 440, 441, 443, 445, 447, 448,
      464, 474, 476, 478, 480, 482, 485, 486, 493, 494, 506, 508, 509,
      515, 526, 529, 531
<223> OTHER INFORMATION: n = A,T,C or G
<220> FEATURE:
<221> NAME/KEY: misc_feature
<222> LOCATION: 8, 23, 27, 50, 92, 131, 137, 150, 151, 152, 153, 159,
      162, 188, 189, 190, 191, 202, 205, 208, 213, 218, 225, 227, 242,
      243, 245, 249, 259, 282, 302, 313, 321, 331, 332, 340, 341,
      344, 345, 346, 359, 363, 396, 404, 406, 414, 417, 421
<223> OTHER INFORMATION: n = A,T,C or G
<220> FEATURE:
<221> NAME/KEY: misc_feature
<222> LOCATION: 422, 430, 435, 436, 439, 440, 441, 443, 445, 447, 448,
      464, 474, 476, 478, 480, 482, 485, 486, 493, 494, 506, 508, 509,
      515, 526, 529, 531
```

<223> OTHER INFORMATION: n = A,T,C or G

<400> SEQUENCE: 3
gaattcangc gaaggatatg canaagngat gtccacaaga gttcattgan cgctgaaatg 60
aaactctttg ctcaacaatg caaggaggta cnacatcctt atcatcacag cacttattcc 120
aggtaaaaaa nctccanttt tatttaatan nnnaatgant gngtcactga aggaaggttc 180
agttgttnnn nctttacctg cngangcngg cgnaaacntt gatancncct tggggcgaca 240
anncnggtnt cagaggggna attactcaca tcggcgagag gngagctggc cacggggggg 300
gncactcagg ccngcaccct ngattccaac nncatcaccn nacnnntgaa ggccatcanc 360
ccngacaaag atacttttta ttttgatgtg aaagangact ttcncnttgg tacnatnggt 420
nntttccatn tcggnnctnn ngngntnnaa ggtggtaaag gaanttttcc cccngncntn 480
cnggnncccg tgnnccccac cgtccngnnc ttcgnccgcc ccactnctnt nc 532

<210> SEQ ID NO 4
<211> LENGTH: 743
<212> TYPE: DNA
<213> ORGANISM: Homo Sapien
<220> FEATURE:
<221> NAME/KEY: misc_feature
<222> LOCATION: 12, 80, 112, 114, 118, 119, 120, 128, 129, 133, 138, 155, 169, 173, 175, 176, 200, 229, 230, 232, 233, 237, 246, 254, 258, 271, 279, 281, 284, 295, 302, 310, 312, 317, 320, 323, 344, 347, 352, 367, 377, 397, 399, 401, 405, 406, 408
<223> OTHER INFORMATION: n = A,T,C or G
<220> FEATURE:
<221> NAME/KEY: misc_feature
<222> LOCATION: 415, 418, 421, 429, 438, 445, 446, 447, 450, 451, 456, 458, 466, 473, 485, 489, 491, 492, 503, 505, 509, 511, 512, 515, 517, 523, 530, 533, 538, 555, 560, 570, 580, 583, 584, 593, 605, 607, 625, 626, 632, 636, 639, 640, 644, 645, 648
<223> OTHER INFORMATION: n = A,T,C or G
<220> FEATURE:
<221> NAME/KEY: misc_feature
<222> LOCATION: 654, 670, 672, 674, 677, 680, 683, 690, 705, 714, 718, 721, 728, 734, 736, 737, 739
<223> OTHER INFORMATION: n = A,T,C or G
<220> FEATURE:
<221> NAME/KEY: misc_feature
<222> LOCATION: 12, 80, 112, 114, 118, 119, 120, 128, 129, 133, 138, 155, 169, 173, 175, 176, 200, 229, 230, 232, 233, 237, 246, 254, 258, 271, 279, 281, 284, 295, 302, 310, 312, 317, 320, 323, 344, 347, 352, 367, 377, 397, 399, 401, 405, 406, 408
<223> OTHER INFORMATION: n = A,T,C or G
<220> FEATURE:
<221> NAME/KEY: misc_feature
<222> LOCATION: 415, 418, 421, 429, 438, 445, 446, 447, 450, 451, 456, 458, 466, 473, 485, 489, 491, 492, 503, 505, 509, 511, 512, 515, 517, 523, 530, 533, 538, 555, 560, 570, 580, 583, 584, 593, 605, 607, 625, 626, 632, 636, 639, 640, 644, 645, 648
<223> OTHER INFORMATION: n = A,T,C or G
<220> FEATURE:
<221> NAME/KEY: misc_feature
<222> LOCATION: 654, 670, 672, 674, 677, 680, 683, 690, 705, 714, 718, 721, 728, 734, 736, 737, 739
<223> OTHER INFORMATION: n = A,T,C or G

<400> SEQUENCE: 4
gaattcaagc anactttggg gaaaaggagg ttcttaaaat cagtgtttcc cctttgtgca 60
cttgtagaaa aaaaagaaan accttctaga gctgatttga tggacaatgg ananagcnnn 120
ccctgtgnnt atnataangg aagctagctg ctctncggtc acctttgcnt agnannatac 180
tttaacctgg cttttacagn agtagtaact gccctccaac cgtcttaann gnnaatntcg 240
gagccnattg cgcngtgntc cacctacggc naatatttnc nccnaggagg atggntttcc 300
cngccagtan tnccttngcn ttnaacctca cgtgaccttc ttangcnatt cncgctcgcc 360

-continued gcaagangtc tttgttnttc ccttctcgca ctccttntnt ntctnngngc cgtgncgncc 420
ncttccttnc gctgaccngg ctcgnnnctn nttgcncntt cagggngctc ttnccaagct 480
cctcngggnt nntgcatttt ttncncccng nntgncngcc ccnccgcccn gcncctgntt 540
cagccttaca cttcnggcan cggcctacan ggggataaan canncatttg tcncgggcgt 600
ttacntnctc ccgtcccacc atctnngcca tnttcnccnn gggnngtnct tttnctacct 660
cccccccccn cncnctncan tcntttaccn gttcgcgctc ctctntgcgt tcgngccncc 720
ncgtcgcnct tttncnncnc ttt 743

<210> SEQ ID NO 5
<211> LENGTH: 714
<212> TYPE: DNA
<213> ORGANISM: Homo Sapien
<220> FEATURE:
<221> NAME/KEY: misc_feature
<222> LOCATION: 548, 565, 566, 568, 654, 664, 681, 694
<223> OTHER INFORMATION: n = A,T,C or G
<220> FEATURE:
<221> NAME/KEY: misc_feature
<222> LOCATION: 548, 565, 566, 568, 654, 664, 681, 694
<223> OTHER INFORMATION: n = A,T,C or G

<400> SEQUENCE: 5
gaattcaagc ggaacgctca cggactgtgt ggtaatgaga gatccaaaca ccaagcgctc 60
caggggcttt gggtttgtca catatgccac tgtggaggag gtggatgcag ctatgaatgc 120
aaggccacac aaggtggatg gaagagttgt ggaaccaaag agagctgtct ccagagaaga 180
ttctcaaaga ccaggtgccc acttaactgt gaaaaagata tttgttggtg gcattaaaga 240
agacactgaa gaacatcacc taagagatta ttttgaacag tatggaaaaa ttgaagtgat 300
tgaaatcatg actgaccgag gcagtggcaa gaaaaggggc tttgcctttg taacctttga 360
cgaccatgac tccgtggata agattgtcat tcagaaatac catactgtga atggccacaa 420
ctgtgaagtt agaaaagccc tgtcaaagca agagatggct agtgcttcat ccaaccaaag 480
aggtcgaagt ggttctggaa actttggtgg tggtcgtgga ggtggtttca gtgggaatga 540
caacttcngt cctggaggaa acttnnantg gtcctggtgg ctttggtggc aaccgtggtg 600
gtggtggata tggtggcaat ggggatggct ataatggatt tggtatgatg gaancaattt 660
tggnggtggt ggaagctaca ntgattttgg gaantaaaac aatcaatcct caaa 714

<210> SEQ ID NO 6
<211> LENGTH: 294
<212> TYPE: DNA
<213> ORGANISM: Homo Sapien
<220> FEATURE:
<221> NAME/KEY: misc_feature
<222> LOCATION: 8, 259, 266, 270, 273, 278
<223> OTHER INFORMATION: n = A,T,C or G
<220> FEATURE:
<221> NAME/KEY: misc_feature
<222> LOCATION: 8, 259, 266, 270, 273, 278
<223> OTHER INFORMATION: n = A,T,C or G

<400> SEQUENCE: 6
aaattcangc gttatcgtcc tttcttccat tcttaacagt atgtgcccat ttgcaaaaca 60
aaaatgctaa taatcagtaa tagtcctata aaagatgtta actctgttta gtcattgact 120
gatcttgctc taaccttaaa attttgtgat tattgacctc tgttgcattt attctaaagc 180
cccccgaagc ttgcggccgc actcgagtaa ctagttaacc ccttggggcc tctaaacggg 240
tcttgagggg taacttggnt cctcgngggn ggnggcangc ttcggggggg tttg 294

<210> SEQ ID NO 7
<211> LENGTH: 705
<212> TYPE: DNA
<213> ORGANISM: Homo Sapien
<220> FEATURE:
<221> NAME/KEY: misc_feature
<222> LOCATION: 547, 564, 575, 626, 641, 676
<223> OTHER INFORMATION: n = A,T,C or G
<220> FEATURE:
<221> NAME/KEY: misc_feature
<222> LOCATION: 547, 564, 575, 626, 641, 676
<223> OTHER INFORMATION: n = A,T,C or G

<400> SEQUENCE: 7

```
gaattcaagc aagacaagga tgaaaagaag aaggggagg atgaagacaa aggtcctccc     60

tgtggcccag tgaactgcaa tgaaaagatc gtggtccttc tgcagcgctt gaagcctgag    120

atcaaggatg tcattgagca gctcaacctg gtcaccacct ggttgcagct gcagatacct    180

cggattgagg atggtaacaa ttttggagtg gctgtccagg agaaggtgtt tgagctgatg    240

accagcctcc acaccaagct agaaggcttc cacactcaaa tctctaagta tttctctgag    300

cgtggtgatg cagtgactaa agcagccaag cagccccatg tgggtgatta tcggcagctg    360

gtgcacgagc tggatgaggc agagtaccgg gacatccggc tgatggtcat ggagatccgc    420

aatgcttatg ctgtgttata tgacatcatc ctgaagaact tcgagaagct caagaagccc    480

aggggagaaa caaagggaat gatctattga gagccctctc tcccattctg tgatgagtac    540

agcaganacc ttcctgcttt ttantgggga cccanatttt ccccaaactt gctctgttga    600

gatttttccc tcaccttgcc tctcangcac aataaatata nttataccac tgccaaagct    660

tgcgggcgca ctccantaac tagttaaccc cttggggcct ctaaa                   705
```

<210> SEQ ID NO 8
<211> LENGTH: 657
<212> TYPE: DNA
<213> ORGANISM: Homo Sapien
<220> FEATURE:
<221> NAME/KEY: misc_feature
<222> LOCATION: 449, 461, 503, 514, 517, 524, 534, 544, 553, 555, 559,
561, 564, 570, 576, 579, 582, 583, 591, 616, 621, 628, 629, 631,
634, 635, 644, 651, 656
<223> OTHER INFORMATION: n = A,T,C or G
<220> FEATURE:
<221> NAME/KEY: misc_feature
<222> LOCATION: 449, 461, 503, 514, 517, 524, 534, 544, 553, 555, 559,
561, 564, 570, 576, 579, 582, 583, 591, 616, 621, 628, 629, 631,
634, 635, 644, 651, 656
<223> OTHER INFORMATION: n = A,T,C or G

<400> SEQUENCE: 8

```
gaattctcaa aatagttcag aaaaatcatg tttcaaagta ctcacattct tccagatgag     60

gaaaaaatgg tgaaggaaag aaaaaggaaa ttgaaagaag tattaatcca aactttcaaa    120

gaaaatcaac agtgtcaaaa acggtatttc gctgcctggc acaagctgat tcttgatcat    180

aggattaagc tggggaaagc tgggaccctg tctgactgga agattcagct gaaggtcctg    240

cgggcctgga gagactacac aagattccag aagttggagc gggagactca agccttggaa    300

aatgatctta gggaagaaaa cagaaaacaa caactggcca ctgagtataa ccggaaacaa    360

gttctccgac actgctttac agaatggcag cattggcatg gcgccgagct cctgaagaga    420

gagctggctc tcacaaaaga ggaaactang aagaagatgg ntgcactgct gcaggcagca    480

tcactgggga aactcagtgc cantgggtta tcangcntca gtcnacctga gganggaaca    540

gccntggtgg gtncnccant naanaatggn cagganacng cnntgccccc ntttgtggga    600
```

-continued aaagcccccc ttgggnagca ntgggtgnnt ntcnntcccc cccngggaag nacaana 657

<210> SEQ ID NO 9
<211> LENGTH: 420
<212> TYPE: DNA
<213> ORGANISM: Homo Sapien
<220> FEATURE:
<221> NAME/KEY: misc_feature
<222> LOCATION: 206, 417
<223> OTHER INFORMATION: n = A,T,C or G
<220> FEATURE:
<221> NAME/KEY: misc_feature
<222> LOCATION: 206, 417
<223> OTHER INFORMATION: n = A,T,C or G

<400> SEQUENCE: 9
gaattctgga aagttgggta caactgtgaa gccaaagagt ctggttactt caagttctgg 60
ggctttaaaa aagcagcata agaagccctt tgatgcaatg aataacattg tggcaaattt 120
gctcctcaac ctaacgaggg aagcttgcgg ccgcactcga gtaactagtt aaccccttgg 180
ggcctctaaa cgggtcttga ggggtntact aagttactcg agtgcggccg caagcttccc 240
tcgttaggtt gaggagcaaa tttgccacaa tgttattcat tgcatcaaag ggcttcttat 300
gctgcttttt taaagcccca gaacttgaag taaccagact ctttggcttc acagttgtac 360
ccaactttcc agaattcgga tccccgagca tcacacctga ctggaatacg acagctncaa 420

<210> SEQ ID NO 10
<211> LENGTH: 160
<212> TYPE: PRT
<213> ORGANISM: Homo Sapien
<220> FEATURE:
<221> NAME/KEY: VARIANT
<222> LOCATION: 1, 9
<223> OTHER INFORMATION: Xaa = Any Amino Acid
<220> FEATURE:
<221> NAME/KEY: VARIANT
<222> LOCATION: 1, 9
<223> OTHER INFORMATION: Xaa = Any Amino Acid

<400> SEQUENCE: 10

```
Xaa Asn Ser Ser Lys Val Phe Ile Xaa Thr Arg His Thr Pro Arg Glu
 1               5                  10                  15

Ser Asn Met Lys Ser Ala Ala Val Leu Ala Leu Gly Phe Ile Phe Leu
            20                  25                  30

Phe Thr Val Gly Gly Leu Thr Gly Ile Val Leu Ala Asn Ser Ser Leu
        35                  40                  45

Asp Ile Val Leu His Asp Thr Tyr Tyr Val Val Ala His Phe His Tyr
    50                  55                  60

Val Leu Ser Ile Gly Ala Val Phe Ala Ile Ile Gly Gly Phe Ile His
65                  70                  75                  80

Phe Pro Leu Phe Ser Gly Tyr Thr Leu Asp Gln Thr Tyr Ala Lys Ile
                85                  90                  95

His Phe Thr Ile Ile Phe Ile Gly Val Asn Leu Thr Phe Phe Pro Gln
            100                 105                 110

His Phe Leu Gly Leu Thr Gly Met Pro Arg Arg Tyr Ser Asp Tyr Pro
        115                 120                 125

Asp Ala Tyr Thr Thr Asn Ile Leu Ser Ser Val Gly Ser Ser Leu Arg
    130                 135                 140

Pro His Ser Ser Asn Phe Thr Pro Trp Gly Leu Thr Gly Leu Glu Gly
145                 150                 155                 160
```

<210> SEQ ID NO 11

<211> LENGTH: 152
<212> TYPE: PRT
<213> ORGANISM: Homo Sapien
<220> FEATURE:
<221> NAME/KEY: VARIANT
<222> LOCATION: 1, 9
<223> OTHER INFORMATION: Xaa = Any Amino Acid
<220> FEATURE:
<221> NAME/KEY: VARIANT
<222> LOCATION: 1, 9
<223> OTHER INFORMATION: Xaa = Any Amino Acid

<400> SEQUENCE: 11

```
Xaa Ile Gln Ala Lys Tyr Leu Ser Xaa Leu Ala Thr Leu His Gly Lys
 1               5                  10                  15

Ala Ile Asn Asp Leu Leu Gln Cys Ser Glu Pro Asp Ser Ser Phe Phe
            20                  25                  30

Ser Pro Val Ala Leu Ala Leu Tyr Gln Thr His His Thr Ser Tyr Tyr
        35                  40                  45

Thr Thr Arg Thr Thr Leu Leu Thr Ser Thr Met Ser Tyr Gln Glu Leu
    50                  55                  60

Tyr Leu Pro Ser Glu Ala Ser Phe Ile Asp Phe Pro Tyr Ser Gln Ala
65                  70                  75                  80

Thr Pro Thr Lys Pro Thr Pro Lys Ser Ile Ser Leu Ser Tyr Ser Ser
                85                  90                  95

Ala Ile Leu Ser Ser His Asn Thr Phe Ser Ala Pro Glu Cys Pro Asp
            100                 105                 110

Val Thr Arg Thr Thr Pro Met His Thr Pro His Glu Thr Ser Tyr His
        115                 120                 125

Leu Ala Gln Ala Cys Gly Arg Thr Arg Val Thr Ser Leu Pro Leu Gly
    130                 135                 140

Ala Ser Lys Arg Val Leu Arg Gly
145                 150
```

<210> SEQ ID NO 12
<211> LENGTH: 163
<212> TYPE: PRT
<213> ORGANISM: Homo Sapien
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 8
<223> OTHER INFORMATION: Xaa = Any Amino Acid

<400> SEQUENCE: 12

```
Glu Phe Lys Gln Ser Ile Tyr Xaa Asp Ser Pro His Ser Thr Gly Lys
 1               5                  10                  15

Gln Tyr Glu Met Ile Cys Cys Ser Ala Leu Ser Pro Arg Ile His Leu
            20                  25                  30

Ser Phe His Arg Arg Trp Pro Asp Trp His Cys Ile Ser Lys Leu Ile
        35                  40                  45

Thr Arg His Arg Thr Thr Arg His Val Leu Arg Cys Ser Ser Leu Pro
    50                  55                  60

Leu Cys Pro Ile Asn Arg Ser Cys Ile Cys His His Arg Arg Leu His
65                  70                  75                  80

Ser Leu Ile Ser Pro Ile Leu Arg Leu His Pro Arg Pro Asn Leu Arg
                85                  90                  95

Gln Asn Pro Phe His Tyr His Ile His Arg Arg Lys Ser Asn Phe Leu
            100                 105                 110
```

-continued

```
Pro Thr Thr Leu Ser Arg Pro Asn Arg Asn Ala Pro Thr Leu Leu Gly
        115                 120                 125

Leu Pro Arg Cys Ile His His Met Lys His Pro Ile Ile Cys Arg Leu
    130                 135                 140

Lys Leu Ala Ala Ala Leu Glu Leu Val Tyr Pro Leu Gly Pro Leu Asn
145                 150                 155                 160

Gly Ser Gly


<210> SEQ ID NO 13
<211> LENGTH: 224
<212> TYPE: PRT
<213> ORGANISM: Homo Sapien
<220> FEATURE:
<221> NAME/KEY: VARIANT
<222> LOCATION: 1, 21, 25, 26, 28, 32, 139, 194
<223> OTHER INFORMATION: Xaa = Any Amino Acid
<220> FEATURE:
<221> NAME/KEY: VARIANT
<222> LOCATION: 1, 21, 25, 26, 28, 32, 139, 194
<223> OTHER INFORMATION: Xaa = Any Amino Acid

<400> SEQUENCE: 13

Xaa Asn Ser Ser Ala Pro Phe Arg Ser Tyr Thr Ser Arg Lys Lys Phe
 1               5                  10                  15

His Gln Ala Ile Xaa Leu Val Ile Xaa Xaa Asn Xaa Thr Lys Asp Xaa
            20                  25                  30

Ser Tyr Leu Lys Tyr Thr Gly Glu Arg Ala Pro Ser Ala Gly Val Pro
        35                  40                  45

Val Ala Tyr Arg Ser Lys Leu Lys Asp Leu Lys Leu Glu Ala Ser Gln
    50                  55                  60

Asp Ala Lys Lys Gly Glu Glu Lys Arg Thr Ile His Lys Phe His Val
65                  70                  75                  80

Tyr Phe Lys Thr Phe Val Pro Leu His Asn Lys Tyr Phe Arg Glu Asn
                85                  90                  95

Tyr His Pro Phe Lys Ile Lys Val Gln Ser Lys Leu Phe Ser Ile Ile
            100                 105                 110

Val Ile Phe Leu Thr Ser Ser Asn Met Ser Gln Tyr Leu Gly Leu Leu
        115                 120                 125

Asp Val Lys Arg Gln Tyr Leu Gly Val Ile Xaa Glu Ile Thr Asn Arg
    130                 135                 140

Gly Ile Leu Asp Cys Ile Leu Ser Ile Leu Ala Phe Met Lys Tyr Arg
145                 150                 155                 160

Gln Ala Ser Leu Leu Ser Ser Arg Gln Cys Asn Ser Gln Gly Lys Gly
                165                 170                 175

Gln Gln Phe Trp Ile Ile Pro Thr Leu Ile Ser Trp Gly Lys Ser Ser
            180                 185                 190

Leu Xaa Lys Val Ser Ser Gln Glu Trp Phe Thr Pro Ser Arg Glu Asp
        195                 200                 205

Met Ser Leu Lys Trp Gly Lys Gly Asn Pro Arg Phe His Ser His Cys
    210                 215                 220


<210> SEQ ID NO 14
<211> LENGTH: 226
<212> TYPE: PRT
<213> ORGANISM: Homo Sapien
<220> FEATURE:
<221> NAME/KEY: VARIANT
<222> LOCATION: 1, 20, 23, 26, 29, 139, 196
<223> OTHER INFORMATION: Xaa = Any Amino Acid
<220> FEATURE:
```

<221> NAME/KEY: VARIANT
<222> LOCATION: 1, 20, 23, 26, 29, 139, 196
<223> OTHER INFORMATION: Xaa = Any Amino Acid

<400> SEQUENCE: 14

```
Xaa Ile Gln Ala His Leu Ser Glu Ala Thr Leu Ala Gly Lys Asn Ser
 1               5                  10                  15

Ile Lys Gln Xaa His Phe Xaa Ile Ile Xaa Gln Lys Xaa Leu Asp Leu
            20                  25                  30

Thr Ser Ile His Glu Gly Lys Glu Pro Pro Gln Gln Val Phe Pro Leu
        35                  40                  45

Leu Thr Glu Ala Asn Arg Thr Asn Trp Arg Gln Ala Arg Met Pro Lys
    50                  55                  60

Arg Gly Lys Arg Asn Asp Lys Glu Pro Phe Ile Asn Ser Met Ser Thr
65                  70                  75                  80

Ser Arg His Leu Ser Asn Asp Pro Tyr Ile Ile Ser Ile Leu Gly Lys
                85                  90                  95

Thr Thr Thr Leu Leu Arg Lys Tyr Asn Leu Lys Ser Cys Ser Ser Gln
            100                 105                 110

Leu Tyr Phe Leu Leu Pro Val Ile Cys Leu Asn Thr Leu Asp Cys Trp
        115                 120                 125

Met Ser Lys Asp Asn Thr Trp Gly Ser Ser Xaa Arg Ser Glu Gln Ile
    130                 135                 140

Glu Glu Phe Ser Arg Thr Val Tyr Ser Leu Phe Trp Leu Phe Glu Ser
145                 150                 155                 160

Thr Asp Arg Leu Leu Cys Tyr Pro Pro Gly Ser Val Ile Val Lys Glu
                165                 170                 175

Lys Gly Asn Ser Phe Gly Ser Phe Leu Arg His Ser Ala Gly Glu Arg
            180                 185                 190

Val His Trp Xaa Lys Cys Pro Pro Lys Asn Gly Leu His Gln Ala Glu
        195                 200                 205

Arg Thr Cys His Asn Gly Glu Arg Glu Thr Pro Val Ser Thr Val Thr
    210                 215                 220

Val Ser
225
```

<210> SEQ ID NO 15
<211> LENGTH: 225
<212> TYPE: PRT
<213> ORGANISM: Homo Sapien
<220> FEATURE:
<221> NAME/KEY: VARIANT
<222> LOCATION: 19, 23, 24, 25, 29, 138, 193
<223> OTHER INFORMATION: Xaa = Any Amino Acid
<220> FEATURE:
<221> NAME/KEY: VARIANT
<222> LOCATION: 19, 23, 24, 25, 29, 138, 193
<223> OTHER INFORMATION: Xaa = Any Amino Acid

<400> SEQUENCE: 15

```
Glu Phe Lys Arg Thr Phe Gln Lys Leu His Gln Glu Lys Ile Pro Ser
 1               5                  10                  15

Ser Asn Xaa Ile Ser Asn Xaa Xaa Xaa His Lys Arg Xaa Leu Ile Leu
            20                  25                  30

Leu Glu Val Tyr Met Arg Gly Lys Ser Pro Leu Ser Arg Cys Ser Arg
        35                  40                  45

Cys Leu Gln Lys Gln Thr Lys Gly Pro Lys Thr Gly Gly Lys Pro Gly
    50                  55                  60

Cys Gln Lys Gly Gly Arg Glu Met Ile Lys Asn His Ser Ile Pro Cys
```

```
65                  70                  75                  80

Leu Leu Gln Asp Ile Cys Leu Met Thr Leu Thr Val Phe Gly Lys Leu
                85                  90                  95

Pro Pro Phe Asp Lys Ser Thr Ile Leu Lys Ala Val Val Leu Asn Tyr
            100                 105                 110

Ser Asn Ile Ser Tyr Phe Gln Tyr Val Ser Ile Pro Trp Thr Ala Gly
        115                 120                 125

Cys Gln Lys Thr Ile Pro Gly Gly His Xaa Asp Leu Asn Lys Arg Asn
    130                 135                 140

Ser Leu Gly Leu Tyr Thr Leu Tyr Phe Gly Phe Leu Asn Glu Val Gln
145                 150                 155                 160

Thr Gly Phe Ser Ala Ile Leu Gln Ala Val Ser Arg Lys Arg Ala Thr
                165                 170                 175

Val Leu Asp His Ser Leu Asp Thr Asn Gln Leu Gly Lys Glu Phe Ile
            180                 185                 190

Xaa Lys Ser Val Leu Pro Arg Met Val Tyr Thr Lys Gln Arg Gly His
        195                 200                 205

Val Thr Glu Met Gly Lys Gly Lys Pro Pro Phe Pro Gln Ser Leu Leu
    210                 215                 220

Ala
225


<210> SEQ ID NO 16
<211> LENGTH: 174
<212> TYPE: PRT
<213> ORGANISM: Homo Sapien
<220> FEATURE:
<221> NAME/KEY: VARIANT
<222> LOCATION: 1, 4, 9, 10, 17, 30, 43, 45, 49, 50, 52, 53, 62, 63, 66,
      67, 68, 70, 72, 74, 75, 80, 81, 82, 85, 93, 100, 103, 106,
      109, 110, 112, 113, 114, 118, 119, 129, 132, 135, 136, 137,
      138, 140, 142, 143, 144, 145, 146, 152, 155, 156, 157
<223> OTHER INFORMATION: Xaa = Any Amino Acid
<220> FEATURE:
<221> NAME/KEY: VARIANT
<222> LOCATION: 158, 159, 161, 162, 166, 167, 169, 172, 173, 174
<223> OTHER INFORMATION: Xaa = Any Amino Acid
<220> FEATURE:
<221> NAME/KEY: VARIANT
<222> LOCATION: 1, 4, 9, 10, 17, 30, 43, 45, 49, 50, 52, 53, 62, 63, 66,
      67, 68, 70, 72, 74, 75, 80, 81, 82, 85, 93, 100, 103, 106,
      109, 110, 112, 113, 114, 118, 119, 129, 132, 135, 136, 137,
      138, 140, 142, 143, 144, 145, 146, 152, 155, 156, 157
<223> OTHER INFORMATION: Xaa = Any Amino Acid
<220> FEATURE:
<221> NAME/KEY: VARIANT
<222> LOCATION: 158, 159, 161, 162, 166, 167, 169, 172, 173, 174
<223> OTHER INFORMATION: Xaa = Any Amino Acid

<400> SEQUENCE: 16

Xaa Asn Ser Xaa Glu Gly Tyr Ala Xaa Xaa Met Ser Thr Arg Val His
 1               5                  10                  15

Xaa Leu Lys Asn Ser Leu Leu Asn Asn Ala Arg Arg Tyr Xaa Ile Leu
            20                  25                  30

Ile Ile Thr Ala Leu Ile Pro Gly Lys Lys Xaa Pro Xaa Leu Phe Asn
        35                  40                  45

Xaa Xaa Met Xaa Xaa Ser Leu Lys Glu Gly Ser Val Val Xaa Xaa Leu
    50                  55                  60

Pro Xaa Xaa Xaa Gly Xaa Asn Xaa Asp Xaa Xaa Leu Gly Arg Gln Xaa
65                  70                  75                  80

Xaa Xaa Gln Arg Xaa Asn Tyr Ser His Arg Arg Glu Xaa Ser Trp Pro
                85                  90                  95
```

```
Arg Gly Gly Xaa Leu Arg Xaa Ala Pro Xaa Ile Pro Xaa Xaa Ser Xaa
            100                 105                 110

Xaa Xaa Arg Pro Ser Xaa Xaa Thr Lys Ile Leu Phe Ile Leu Met Lys
        115                 120                 125

Xaa Thr Phe Xaa Leu Val Xaa Xaa Xaa Xaa Ser Xaa Ser Xaa Xaa Xaa
    130                 135                 140

Xaa Xaa Lys Val Val Lys Glu Xaa Phe Pro Xaa Xaa Xaa Xaa Xaa Pro
145                 150                 155                 160

Xaa Xaa Pro Pro Ser Xaa Xaa Ser Xaa Ala Pro Xaa Xaa Xaa
                165                 170


<210> SEQ ID NO 17
<211> LENGTH: 173
<212> TYPE: PRT
<213> ORGANISM: Homo Sapien
<220> FEATURE:
<221> NAME/KEY: VARIANT
<222> LOCATION: 1, 3, 8, 10, 17, 30, 43, 45, 50, 51, 52, 53, 60, 61, 65,
      66, 67, 69, 70, 73, 78, 79, 81, 84, 92, 98, 102, 105, 108,
      111, 112, 113, 117, 119, 129, 131, 132, 135, 136, 137, 140,
      142, 143, 144, 145, 146, 150, 154, 155, 156, 157, 158
<223> OTHER INFORMATION: Xaa = Any Amino Acid
<220> FEATURE:
<221> NAME/KEY: VARIANT
<222> LOCATION: 160, 164, 165, 167, 171, 172, 173
<223> OTHER INFORMATION: Xaa = Any Amino Acid
<220> FEATURE:
<221> NAME/KEY: VARIANT
<222> LOCATION: 1, 3, 8, 10, 17, 30, 43, 45, 50, 51, 52, 53, 60, 61, 65,
      66, 67, 69, 70, 73, 78, 79, 81, 84, 92, 98, 102, 105, 108,
      111, 112, 113, 117, 119, 129, 131, 132, 135, 136, 137, 140,
      142, 143, 144, 145, 146, 150, 154, 155, 156, 157, 158
<223> OTHER INFORMATION: Xaa = Any Amino Acid
<220> FEATURE:
<221> NAME/KEY: VARIANT
<222> LOCATION: 160, 164, 165, 167, 171, 172, 173
<223> OTHER INFORMATION: Xaa = Any Amino Acid

<400> SEQUENCE: 17

Xaa Ile Xaa Ala Lys Asp Met Xaa Lys Xaa Cys Pro Gln Glu Phe Ile
 1               5                  10                  15

Xaa Arg Asn Glu Thr Leu Cys Ser Thr Met Gln Gly Gly Xaa Thr Ser
            20                  25                  30

Leu Ser Ser Gln His Leu Phe Gln Val Lys Xaa Leu Xaa Phe Tyr Leu
        35                  40                  45

Ile Xaa Xaa Xaa Xaa His Arg Lys Val Gln Leu Xaa Xaa Leu Tyr Leu
    50                  55                  60

Xaa Xaa Xaa Ala Xaa Xaa Leu Ile Xaa Pro Trp Gly Asp Xaa Xaa Gly
65                  70                  75                  80

Xaa Arg Gly Xaa Ile Thr His Ile Gly Glu Arg Xaa Ala Gly His Gly
                85                  90                  95

Gly Xaa His Ser Gly Xaa His Pro Xaa Phe Gln Xaa His His Xaa Xaa
            100                 105                 110

Xaa Glu Gly His Xaa Pro Xaa Gln Arg Tyr Phe Leu Phe Cys Glu Arg
        115                 120                 125

Xaa Leu Xaa Xaa Trp Tyr Xaa Xaa Xaa Phe Pro Xaa Arg Xaa Xaa Xaa
    130                 135                 140

Xaa Xaa Arg Trp Arg Xaa Phe Ser Pro Xaa Xaa Xaa Xaa Xaa Arg Xaa
145                 150                 155                 160

Pro His Arg Xaa Xaa Leu Xaa Pro Pro His Xaa Xaa Xaa
                165                 170


<210> SEQ ID NO 18
```

<211> LENGTH: 174
<212> TYPE: PRT
<213> ORGANISM: Homo Sapien
<220> FEATURE:
<221> NAME/KEY: VARIANT
<222> LOCATION: 3, 8, 9, 17, 31, 43, 45, 48, 49, 51, 52, 61, 62, 66, 67, 68, 69, 71, 72, 73, 78, 79, 80, 84, 91, 98, 102, 104, 108, 111, 112, 113, 117, 118, 129, 132, 133, 135, 136, 138, 141, 142, 143, 144, 145, 146, 147, 152, 155, 156, 157, 158
<223> OTHER INFORMATION: Xaa = Any Amino Acid
<220> FEATURE:
<221> NAME/KEY: VARIANT
<222> LOCATION: 159, 162, 166, 167, 169, 173, 174
<223> OTHER INFORMATION: Xaa = Any Amino Acid
<220> FEATURE:
<221> NAME/KEY: VARIANT
<222> LOCATION: 3, 8, 9, 17, 31, 43, 45, 48, 49, 51, 52, 61, 62, 66, 67, 68, 69, 71, 72, 73, 78, 79, 80, 84, 91, 98, 102, 104, 108, 111, 112, 113, 117, 118, 129, 132, 133, 135, 136, 138, 141, 142, 143, 144, 145, 146, 147, 152, 155, 156, 157, 158
<223> OTHER INFORMATION: Xaa = Any Amino Acid
<220> FEATURE:
<221> NAME/KEY: VARIANT
<222> LOCATION: 159, 162, 166, 167, 169, 173, 174
<223> OTHER INFORMATION: Xaa = Any Amino Acid

<400> SEQUENCE: 18

```
Glu Phe Xaa Arg Arg Ile Cys Xaa Xaa Asp Val His Lys Ser Ser Leu
 1               5                  10                  15

Xaa Ala Glu Met Lys Leu Phe Ala Gln Gln Cys Lys Glu Val Xaa His
            20                  25                  30

Pro Tyr His His Ser Thr Tyr Ser Arg Lys Xaa Ser Xaa Phe Ile Xaa
        35                  40                  45

Xaa Asn Xaa Xaa Val Thr Glu Gly Arg Phe Ser Cys Xaa Xaa Phe Thr
    50                  55                  60

Cys Xaa Xaa Xaa Xaa Lys Xaa Xaa Xaa Leu Gly Ala Thr Xaa Xaa Xaa
65                  70                  75                  80

Ser Glu Gly Xaa Leu Leu Thr Ser Ala Arg Xaa Glu Leu Ala Thr Gly
                85                  90                  95

Gly Xaa Thr Gln Ala Xaa Thr Xaa Asp Ser Asn Xaa Ile Thr Xaa Xaa
            100                 105                 110

Xaa Lys Ala Ile Xaa Xaa Asp Lys Asp Thr Phe Tyr Phe Asp Val Lys
        115                 120                 125

Xaa Asp Phe Xaa Xaa Gly Xaa Xaa Gly Xaa Phe His Xaa Xaa Xaa Xaa
    130                 135                 140

Xaa Xaa Xaa Gly Gly Lys Gly Xaa Phe Pro Xaa Xaa Xaa Xaa Xaa Pro
145                 150                 155                 160

Val Xaa Pro Thr Val Xaa Xaa Phe Xaa Arg Pro Thr Xaa Xaa
                165                 170
```

<210> SEQ ID NO 19
<211> LENGTH: 242
<212> TYPE: PRT
<213> ORGANISM: Homo Sapien
<220> FEATURE:
<221> NAME/KEY: VARIANT
<222> LOCATION: 1, 5, 26, 35, 36, 37, 38, 41, 42, 44, 50, 54, 55, 56, 64, 71, 72, 73, 74, 77, 80, 81, 85, 88, 89, 90, 93, 96, 98, 99, 101, 102, 103, 110, 111, 112, 117, 121, 127, 128, 129, 130, 131, 133, 134, 135, 138, 141, 143, 144, 145, 147, 148
<223> OTHER INFORMATION: Xaa = Any Amino Acid
<220> FEATURE:
<221> NAME/KEY: VARIANT
<222> LOCATION: 150, 153, 157, 158, 159, 163, 165, 166, 167, 169, 172, 173, 174, 180, 182, 185, 188, 189, 190, 193, 197, 203, 204, 206, 207, 208, 210, 211, 213, 218, 219, 220, 221, 222, 223, 225, 230, 233, 234, 235, 238, 240, 241
<223> OTHER INFORMATION: Xaa = Any Amino Acid
<220> FEATURE:
<221> NAME/KEY: VARIANT
<222> LOCATION: 1, 5, 26, 35, 36, 37, 38, 41, 42, 44, 50, 54, 55, 56,
64, 71, 72, 73, 74, 77, 80, 81, 85, 88, 89, 90, 93, 96, 98,
99, 101, 102, 103, 110, 111, 112, 117, 121, 127, 128, 129,
130, 131, 133, 134, 135, 138, 141, 143, 144, 145, 147, 148
<223> OTHER INFORMATION: Xaa = Any Amino Acid
<220> FEATURE:
<221> NAME/KEY: VARIANT
<222> LOCATION: 150, 153, 157, 158, 159, 163, 165, 166, 167, 169, 172,
173, 174, 180, 182, 185, 188, 189, 190, 193, 197, 203, 204, 206,
207, 208, 210, 211, 213, 218, 219, 220, 221, 222, 223, 225,
230, 233, 234, 235, 238, 240, 241
<223> OTHER INFORMATION: Xaa = Any Amino Acid

<400> SEQUENCE: 19

```
Xaa Asn Ser Ser Xaa Leu Trp Gly Lys Gly Gly Ser Asn Gln Cys Phe
 1               5                  10                  15

Pro Phe Val His Leu Lys Lys Lys Lys Xaa Leu Leu Glu Leu Ile Trp
            20                  25                  30

Thr Met Xaa Xaa Xaa Xaa Pro Val Xaa Xaa Ile Xaa Glu Ala Ser Cys
        35                  40                  45

Ser Xaa Val Thr Phe Xaa Xaa Xaa Thr Leu Thr Trp Leu Leu Gln Xaa
    50                  55                  60

Leu Pro Ser Asn Arg Leu Xaa Xaa Xaa Xaa Arg Ser Xaa Leu Arg Xaa
65                  70                  75                  80

Xaa Pro Pro Thr Xaa Asn Ile Xaa Xaa Xaa Glu Asp Xaa Phe Pro Xaa
                85                  90                  95

Gln Xaa Xaa Leu Xaa Xaa Xaa Pro His Val Thr Phe Leu Xaa Xaa Xaa
            100                 105                 110

Arg Ser Pro Gln Xaa Val Phe Val Xaa Pro Phe Ser His Ser Xaa Xaa
        115                 120                 125

Xaa Xaa Xaa Pro Xaa Xaa Xaa Leu Pro Xaa Ala Asp Xaa Ala Xaa Xaa
    130                 135                 140

Xaa Leu Xaa Xaa Gln Xaa Ala Leu Xaa Lys Leu Leu Xaa Xaa Xaa Ala
145                 150                 155                 160

Phe Phe Xaa Pro Xaa Xaa Xaa Ala Xaa Pro Pro Xaa Xaa Xaa Phe Ser
                165                 170                 175

Leu Thr Leu Xaa Ala Xaa Ala Tyr Xaa Gly Ile Xaa Xaa Xaa Phe Val
            180                 185                 190

Xaa Gly Val Tyr Xaa Leu Pro Ser His His Xaa Xaa His Xaa Xaa Xaa
        195                 200                 205

Gly Xaa Xaa Phe Xaa Tyr Leu Pro Pro Xaa Xaa Xaa Xaa Xaa Xaa Tyr
    210                 215                 220

Xaa Phe Ala Leu Leu Xaa Ala Phe Xaa Xaa Xaa Arg Arg Xaa Phe Xaa
225                 230                 235                 240

Xaa Leu
```

<210> SEQ ID NO 20
<211> LENGTH: 242
<212> TYPE: PRT
<213> ORGANISM: Homo Sapien
<220> FEATURE:
<221> NAME/KEY: VARIANT
<222> LOCATION: 1, 5, 27, 36, 37, 38, 39, 41, 42, 43, 44, 49, 54, 55,
56, 63, 73, 74, 76, 79, 81, 83, 87, 90, 91, 95, 97, 100, 101,
102, 103, 104, 110, 111, 113, 118, 121, 128, 129, 131, 132,
134, 135, 136, 139, 142, 144, 145, 146, 148, 151, 153
<223> OTHER INFORMATION: Xaa = Any Amino Acid
<220> FEATURE:
<221> NAME/KEY: VARIANT
<222> LOCATION: 157, 159, 160, 163, 164, 165, 166, 167, 168, 170, 172,
173, 175, 181, 182, 186, 188, 189, 192, 196, 197, 203, 205, 207,

```
      208, 209, 210, 211, 213, 218, 219, 220, 221, 222, 225, 230,
      233, 234, 235, 237, 239, 240, 241
<223> OTHER INFORMATION: Xaa = Any Amino Acid
<220> FEATURE:
<221> NAME/KEY: VARIANT
<222> LOCATION: 1, 5, 27, 36, 37, 38, 39, 41, 42, 43, 44, 49, 54, 55,
      56, 63, 73, 74, 76, 79, 81, 83, 87, 90, 91, 95, 97, 100, 101,
      102, 103, 104, 110, 111, 113, 118, 121, 128, 129, 131, 132,
      134, 135, 136, 139, 142, 144, 145, 146, 148, 151, 153
<223> OTHER INFORMATION: Xaa = Any Amino Acid
<220> FEATURE:
<221> NAME/KEY: VARIANT
<222> LOCATION: 157, 159, 160, 163, 164, 165, 166, 167, 168, 170, 172,
      173, 175, 181, 182, 186, 188, 189, 192, 196, 197, 203, 205, 207,
      208, 209, 210, 211, 213, 218, 219, 220, 221, 222, 225, 230,
      233, 234, 235, 237, 239, 240, 241
<223> OTHER INFORMATION: Xaa = Any Amino Acid

<400> SEQUENCE: 20

Xaa Ile Gln Ala Xaa Phe Gly Glu Lys Glu Val Leu Lys Ile Ser Val
 1               5                  10                  15

Ser Pro Leu Cys Thr Cys Arg Lys Lys Arg Xaa Thr Phe Ser Phe Asp
            20                  25                  30

Gly Gln Trp Xaa Xaa Xaa Xaa Leu Xaa Xaa Xaa Xaa Lys Leu Ala Ala
        35                  40                  45

Xaa Arg Ser Pro Leu Xaa Xaa Xaa Ile Leu Pro Gly Phe Tyr Xaa Ser
    50                  55                  60

Ser Asn Cys Pro Pro Thr Val Leu Xaa Xaa Asn Xaa Gly Ala Xaa Cys
65                  70                  75                  80

Xaa Val Xaa His Leu Arg Xaa Ile Phe Xaa Xaa Arg Arg Met Xaa Phe
                85                  90                  95

Xaa Ala Ser Xaa Xaa Xaa Xaa Xaa Asn Leu Thr Pro Ser Xaa Xaa Ile
            100                 105                 110

Xaa Ala Arg Arg Lys Xaa Ser Leu Xaa Phe Pro Ser Arg Thr Pro Xaa
        115                 120                 125

Xaa Ser Xaa Xaa Arg Xaa Xaa Xaa Phe Leu Xaa Leu Thr Xaa Leu Xaa
    130                 135                 140

Xaa Xaa Cys Xaa Phe Arg Xaa Leu Xaa Pro Ser Ser Xaa Gly Xaa Xaa
145                 150                 155                 160

His Phe Xaa Xaa Xaa Xaa Xaa Xaa Pro Xaa Arg Xaa Xaa Pro Xaa Ser
                165                 170                 175

Ala Leu His Phe Xaa Xaa Arg Pro Thr Xaa Gly Xaa Xaa His Leu Xaa
            180                 185                 190

Arg Ala Phe Xaa Xaa Ser Arg Pro Thr Ile Xaa Ala Xaa Phe Xaa Xaa
        195                 200                 205

Xaa Xaa Xaa Phe Xaa Thr Ser Pro Pro Xaa Xaa Xaa Xaa Xaa Phe Thr
    210                 215                 220

Xaa Ser Arg Ser Ser Xaa Arg Ser Xaa Xaa Xaa Val Xaa Leu Xaa Xaa
225                 230                 235                 240

Xaa Phe


<210> SEQ ID NO 21
<211> LENGTH: 244
<212> TYPE: PRT
<213> ORGANISM: Homo Sapien
<220> FEATURE:
<221> NAME/KEY: VARIANT
<222> LOCATION: 4, 27, 38, 40, 43, 45, 46, 51, 56, 57, 58, 66, 75, 76,
      77, 80, 83, 84, 89, 91, 92, 93, 97, 99, 102, 104, 105, 106,
      113, 114, 116, 121, 124, 131, 132, 133, 134, 137, 138, 139,
      141, 143, 146, 147, 148, 149, 150, 153, 155, 159, 160, 161
<223> OTHER INFORMATION: Xaa = Any Amino Acid
<220> FEATURE:
```

<221> NAME/KEY: VARIANT
<222> LOCATION: 165, 166, 167, 168, 169, 170, 172, 174, 175, 177, 182, 184, 187, 191, 192, 195, 199, 200, 206, 208, 209, 210, 211, 212, 213, 215, 221, 222, 223, 224, 225, 227, 232, 235, 237, 238, 240, 242, 243, 244
<223> OTHER INFORMATION: Xaa = Any Amino Acid
<220> FEATURE:
<221> NAME/KEY: VARIANT
<222> LOCATION: 4, 27, 38, 40, 43, 45, 46, 51, 56, 57, 58, 66, 75, 76, 77, 80, 83, 84, 89, 91, 92, 93, 97, 99, 102, 104, 105, 106, 113, 114, 116, 121, 124, 131, 132, 133, 134, 137, 138, 139, 141, 143, 146, 147, 148, 149, 150, 153, 155, 159, 160, 161
<223> OTHER INFORMATION: Xaa = Any Amino Acid
<220> FEATURE:
<221> NAME/KEY: VARIANT
<222> LOCATION: 165, 166, 167, 168, 169, 170, 172, 174, 175, 177, 182, 184, 187, 191, 192, 195, 199, 200, 206, 208, 209, 210, 211, 212, 213, 215, 221, 222, 223, 224, 225, 227, 232, 235, 237, 238, 240, 242, 243, 244
<223> OTHER INFORMATION: Xaa = Any Amino Acid

<400> SEQUENCE: 21

```
Glu Phe Lys Xaa Thr Leu Gly Lys Arg Arg Phe Leu Lys Ser Val Phe
 1               5                  10                  15

Pro Leu Cys Ala Leu Val Glu Lys Lys Glu Xaa Pro Ser Arg Ala Asp
            20                  25                  30

Leu Met Asp Asn Gly Xaa Ser Xaa Pro Cys Xaa Tyr Xaa Xaa Gly Ser
        35                  40                  45

Leu Leu Xaa Gly His Leu Cys Xaa Xaa Xaa Tyr Phe Asn Leu Ala Phe
    50                  55                  60

Thr Xaa Val Val Thr Ala Leu Gln Pro Ser Xaa Xaa Xaa Ser Glu Xaa
65                  70                  75                  80

Ile Ala Xaa Xaa Ser Thr Tyr Gly Xaa Tyr Xaa Xaa Xaa Gly Gly Trp
                85                  90                  95

Xaa Ser Xaa Pro Val Xaa Pro Xaa Xaa Xaa Thr Ser Arg Asp Leu Leu
            100                 105                 110

Xaa Xaa Phe Xaa Leu Ala Ala Arg Xaa Leu Cys Xaa Ser Leu Leu Ala
        115                 120                 125

Leu Leu Xaa Xaa Xaa Xaa Ala Val Xaa Xaa Xaa Ser Xaa Arg Xaa Gly
    130                 135                 140

Ser Xaa Xaa Xaa Xaa Xaa Ser Gly Xaa Ser Xaa Gln Ala Pro Xaa Xaa
145                 150                 155                 160

Xaa Cys Ile Phe Xaa Xaa Xaa Xaa Xaa Xaa Pro Xaa Ala Xaa Xaa Leu
                165                 170                 175

Xaa Gln Pro Tyr Thr Xaa Gly Xaa Gly Leu Xaa Gly Asp Lys Xaa Xaa
            180                 185                 190

Ile Cys Xaa Gly Arg Leu Xaa Xaa Pro Val Pro Pro Ser Xaa Pro Xaa
        195                 200                 205

Xaa Xaa Xaa Xaa Xaa Leu Xaa Leu Pro Pro Pro Pro Xaa Xaa Xaa Xaa
    210                 215                 220

Xaa Leu Xaa Val Arg Ala Pro Xaa Cys Val Xaa Ala Xaa Xaa Ser Xaa
225                 230                 235                 240

Phe Xaa Xaa Xaa
```

<210> SEQ ID NO 22
<211> LENGTH: 236
<212> TYPE: PRT
<213> ORGANISM: Homo Sapien
<220> FEATURE:
<221> NAME/KEY: VARIANT
<222> LOCATION: 1, 184, 189, 190, 218, 221, 227, 231
<223> OTHER INFORMATION: Xaa = Any Amino Acid
<220> FEATURE:

<221> NAME/KEY: VARIANT
<222> LOCATION: 1, 184, 189, 190, 218, 221, 227, 231
<223> OTHER INFORMATION: Xaa = Any Amino Acid

<400> SEQUENCE: 22

```
Xaa Asn Ser Ser Gly Thr Leu Thr Asp Cys Val Val Met Arg Asp Pro
 1               5                  10                  15

Asn Thr Lys Arg Ser Arg Gly Phe Gly Phe Val Thr Tyr Ala Thr Val
            20                  25                  30

Glu Glu Val Asp Ala Ala Met Asn Ala Arg Pro His Lys Val Asp Gly
        35                  40                  45

Arg Val Val Glu Pro Lys Arg Ala Val Ser Arg Glu Asp Ser Gln Arg
    50                  55                  60

Pro Gly Ala His Leu Thr Val Lys Lys Ile Phe Val Gly Gly Ile Lys
65                  70                  75                  80

Glu Asp Thr Glu Glu His His Leu Arg Asp Tyr Phe Glu Gln Tyr Gly
                85                  90                  95

Lys Ile Glu Val Ile Glu Ile Met Thr Asp Arg Gly Ser Gly Lys Lys
            100                 105                 110

Arg Gly Phe Ala Phe Val Thr Phe Asp Asp His Asp Ser Val Asp Lys
        115                 120                 125

Ile Val Ile Gln Lys Tyr His Thr Val Asn Gly His Asn Cys Glu Val
    130                 135                 140

Arg Lys Ala Leu Ser Lys Gln Glu Met Ala Ser Ala Ser Ser Asn Gln
145                 150                 155                 160

Arg Gly Arg Ser Gly Ser Gly Asn Phe Gly Gly Gly Arg Gly Gly Gly
                165                 170                 175

Phe Ser Gly Asn Asp Asn Phe Xaa Pro Gly Gly Asn Xaa Xaa Trp Ser
            180                 185                 190

Trp Trp Leu Trp Trp Gln Pro Trp Trp Trp Trp Ile Trp Trp Gln Trp
        195                 200                 205

Gly Trp Leu Trp Ile Trp Tyr Asp Gly Xaa Asn Phe Xaa Gly Gly Gly
    210                 215                 220

Ser Tyr Xaa Asp Phe Gly Xaa Asn Asn Gln Ser Ser
225                 230                 235
```

<210> SEQ ID NO 23
<211> LENGTH: 228
<212> TYPE: PRT
<213> ORGANISM: Homo Sapien
<220> FEATURE:
<221> NAME/KEY: VARIANT
<222> LOCATION: 1, 173, 179, 180, 209, 212, 218, 222
<223> OTHER INFORMATION: Xaa = Any Amino Acid
<220> FEATURE:
<221> NAME/KEY: VARIANT
<222> LOCATION: 1, 173, 179, 180, 209, 212, 218, 222
<223> OTHER INFORMATION: Xaa = Any Amino Acid

<400> SEQUENCE: 23

```
Xaa Ile Gln Ala Glu Arg Ser Arg Thr Val Trp Glu Ile Gln Thr Pro
 1               5                  10                  15

Ser Ala Pro Gly Ala Leu Gly Leu Ser His Met Pro Leu Trp Arg Arg
            20                  25                  30

Trp Met Gln Leu Met Gln Gly His Thr Arg Trp Met Glu Glu Leu Trp
        35                  40                  45

Asn Gln Arg Glu Leu Ser Pro Glu Lys Ile Leu Lys Asp Gln Val Pro
    50                  55                  60

Thr Leu Lys Arg Tyr Leu Leu Val Ala Leu Lys Lys Thr Leu Lys Asn
```

```
65                  70                  75                  80

Ile Thr Glu Ile Ile Leu Asn Ser Met Glu Lys Leu Lys Leu Lys Ser
                85                  90                  95

Leu Thr Glu Ala Val Ala Arg Lys Gly Ala Leu Pro Leu Pro Leu Thr
            100                 105                 110

Thr Met Thr Pro Trp Ile Arg Leu Ser Phe Arg Asn Thr Ile Leu Met
        115                 120                 125

Ala Thr Thr Val Lys Leu Glu Lys Pro Cys Gln Ser Lys Arg Trp Leu
    130                 135                 140

Val Leu His Pro Thr Lys Glu Val Glu Val Val Leu Glu Thr Leu Val
145                 150                 155                 160

Val Val Val Glu Val Val Ser Val Gly Met Thr Thr Xaa Val Leu Glu
                165                 170                 175

Glu Thr Xaa Xaa Gly Pro Gly Gly Phe Gly Gly Asn Arg Gly Gly Gly
            180                 185                 190

Gly Tyr Gly Gly Asn Gly Asp Gly Tyr Asn Gly Phe Gly Met Met Glu
        195                 200                 205

Xaa Ile Leu Xaa Val Val Glu Ala Thr Xaa Ile Leu Gly Xaa Lys Thr
    210                 215                 220

Ile Asn Pro Gln
225


<210> SEQ ID NO 24
<211> LENGTH: 223
<212> TYPE: PRT
<213> ORGANISM: Homo Sapien
<220> FEATURE:
<221> NAME/KEY: VARIANT
<222> LOCATION: 170, 176, 177, 204, 208, 213, 217
<223> OTHER INFORMATION: Xaa = Any Amino Acid
<220> FEATURE:
<221> NAME/KEY: VARIANT
<222> LOCATION: 170, 176, 177, 204, 208, 213, 217
<223> OTHER INFORMATION: Xaa = Any Amino Acid

<400> SEQUENCE: 24

Glu Phe Lys Arg Asn Ala His Gly Leu Cys Gly Asn Glu Arg Ser Lys
 1               5                  10                  15

His Gln Ala Leu Gln Gly Leu Trp Val Cys His Ile Cys His Cys Gly
            20                  25                  30

Gly Gly Gly Cys Ser Tyr Glu Cys Lys Ala Thr Gln Gly Gly Trp Lys
        35                  40                  45

Ser Cys Gly Thr Lys Glu Ser Cys Leu Gln Arg Arg Phe Ser Lys Thr
    50                  55                  60

Arg Cys Pro Leu Asn Cys Glu Lys Asp Ile Cys Trp Trp His Arg Arg
65                  70                  75                  80

His Arg Thr Ser Pro Lys Arg Leu Phe Thr Val Trp Lys Asn Ser Asp
                85                  90                  95

Asn His Asp Pro Arg Gln Trp Gln Glu Lys Gly Leu Cys Leu Cys Asn
            100                 105                 110

Leu Arg Pro Leu Arg Gly Asp Cys His Ser Glu Ile Pro Tyr Cys Glu
        115                 120                 125

Trp Pro Gln Leu Ser Lys Ser Pro Val Lys Ala Arg Asp Gly Cys Phe
    130                 135                 140

Ile Gln Pro Lys Arg Ser Lys Trp Phe Trp Lys Leu Trp Trp Trp Ser
145                 150                 155                 160

Trp Arg Trp Phe Gln Trp Glu Gln Leu Xaa Ser Trp Arg Lys Leu Xaa
                165                 170                 175
```

```
Xaa Val Leu Val Ala Leu Val Ala Thr Val Val Val Val Asp Met Val
            180                 185                 190

Ala Met Gly Met Ala Ile Met Asp Leu Val Trp Xaa Gln Phe Trp Xaa
        195                 200                 205

Trp Trp Lys Leu Xaa Phe Trp Glu Xaa Lys Gln Ser Ile Leu Lys
    210                 215                 220


<210> SEQ ID NO 25
<211> LENGTH: 89
<212> TYPE: PRT
<213> ORGANISM: Homo Sapien
<220> FEATURE:
<221> NAME/KEY: VARIANT
<222> LOCATION: 1, 4, 78, 81, 82, 83, 85
<223> OTHER INFORMATION: Xaa = Any Amino Acid
<220> FEATURE:
<221> NAME/KEY: VARIANT
<222> LOCATION: 1, 4, 78, 81, 82, 83, 85
<223> OTHER INFORMATION: Xaa = Any Amino Acid

<400> SEQUENCE: 25

Xaa Asn Ser Xaa Val Ile Val Leu Ser Ser Ile Leu Asn Ser Met Cys
 1               5                  10                  15

Pro Phe Ala Lys Gln Lys Cys Ser Val Ile Val Leu Lys Met Leu Thr
            20                  25                  30

Leu Phe Ser His Leu Ile Leu Leu Pro Asn Phe Val Ile Ile Asp Leu
        35                  40                  45

Cys Cys Ile Tyr Ser Lys Ala Pro Arg Ser Leu Arg Pro His Ser Ser
    50                  55                  60

Asn Leu Thr Pro Trp Gly Leu Thr Gly Leu Glu Gly Leu Xaa Ser Ser
65                  70                  75                  80

Xaa Xaa Xaa Ala Xaa Phe Gly Gly Val
                85


<210> SEQ ID NO 26
<211> LENGTH: 92
<212> TYPE: PRT
<213> ORGANISM: Homo Sapien
<220> FEATURE:
<221> NAME/KEY: VARIANT
<222> LOCATION: 1, 3, 81, 83, 85, 86, 87
<223> OTHER INFORMATION: Xaa = Any Amino Acid
<220> FEATURE:
<221> NAME/KEY: VARIANT
<222> LOCATION: 1, 3, 81, 83, 85, 86, 87
<223> OTHER INFORMATION: Xaa = Any Amino Acid

<400> SEQUENCE: 26

Xaa Ile Xaa Ala Leu Ser Ser Phe Leu Pro Phe Leu Thr Val Cys Ala
 1               5                  10                  15

His Leu Gln Asn Lys Asn Ala Asn Asn Gln Ser Tyr Lys Arg Cys Leu
            20                  25                  30

Cys Leu Val Ile Asp Ser Cys Ser Asn Leu Lys Ile Leu Leu Leu Thr
        35                  40                  45

Ser Val Ala Phe Ile Leu Lys Pro Pro Glu Ala Cys Gly Arg Thr Arg
    50                  55                  60

Val Thr Ser Pro Leu Gly Ala Ser Lys Arg Val Leu Arg Gly Asn Leu
65                  70                  75                  80

Xaa Pro Xaa Gly Xaa Xaa Xaa Ala Ser Gly Gly Phe
                85                  90


<210> SEQ ID NO 27
```

```
<211> LENGTH: 92
<212> TYPE: PRT
<213> ORGANISM: Homo Sapien
<220> FEATURE:
<221> NAME/KEY: VARIANT
<222> LOCATION: 3, 81, 83, 84, 85, 87
<223> OTHER INFORMATION: Xaa = Any Amino Acid
<220> FEATURE:
<221> NAME/KEY: VARIANT
<222> LOCATION: 3, 81, 83, 84, 85, 87
<223> OTHER INFORMATION: Xaa = Any Amino Acid

<400> SEQUENCE: 27

Lys Phe Xaa Arg Tyr Arg Pro Phe Phe His Ser Gln Tyr Val Pro Ile
 1              5                   10                  15

Cys Lys Thr Lys Met Leu Ile Ile Ser Asn Ser Pro Ile Lys Asp Val
            20                  25                  30

Asn Ser Val Ser Leu Thr Asp Leu Ala Leu Thr Leu Lys Phe Cys Asp
        35                  40                  45

Tyr Pro Leu Leu His Leu Phe Ser Pro Pro Lys Leu Ala Ala Ala Leu
    50                  55                  60

Glu Leu Val Asn Pro Leu Gly Pro Leu Asn Gly Ser Gly Val Thr Trp
65                  70                  75                  80

Xaa Leu Xaa Xaa Xaa Gly Xaa Leu Arg Gly Gly Leu
                85                  90


<210> SEQ ID NO 28
<211> LENGTH: 225
<212> TYPE: PRT
<213> ORGANISM: Homo Sapien
<220> FEATURE:
<221> NAME/KEY: VARIANT
<222> LOCATION: 1, 174, 180, 184, 201, 206, 217
<223> OTHER INFORMATION: Xaa = Any Amino Acid
<220> FEATURE:
<221> NAME/KEY: VARIANT
<222> LOCATION: 1, 174, 180, 184, 201, 206, 217
<223> OTHER INFORMATION: Xaa = Any Amino Acid

<400> SEQUENCE: 28

Xaa Asn Ser Ser Lys Thr Arg Met Lys Arg Arg Arg Gly Arg Met Lys
 1              5                   10                  15

Thr Lys Val Leu Pro Val Ala Gln Thr Ala Met Lys Arg Ser Trp Ser
            20                  25                  30

Phe Cys Ser Ala Ser Leu Arg Ser Arg Met Ser Leu Ser Ser Ser Thr
        35                  40                  45

Trp Ser Pro Pro Gly Cys Ser Cys Arg Tyr Leu Gly Leu Arg Met Val
    50                  55                  60

Thr Ile Leu Glu Trp Leu Ser Arg Arg Arg Cys Leu Ser Pro Ala Ser
65                  70                  75                  80

Thr Pro Ser Lys Ala Ser Thr Leu Lys Ser Leu Ser Ile Ser Leu Ser
                85                  90                  95

Val Val Met Gln Leu Lys Gln Pro Ser Ser Pro Met Trp Val Ile Ile
            100                 105                 110

Gly Ser Trp Cys Thr Ser Trp Met Arg Gln Ser Thr Gly Thr Ser Gly
        115                 120                 125

Trp Ser Trp Arg Ser Ala Met Leu Met Leu Cys Tyr Met Thr Ser Ser
    130                 135                 140

Arg Thr Ser Arg Ser Ser Arg Ser Pro Gly Glu Lys Gln Arg Glu Ser
145                 150                 155                 160

Ile Glu Ser Pro Leu Ser His Ser Val Met Ser Thr Ala Xaa Thr Phe
                165                 170                 175
```

```
Leu Leu Phe Xaa Gly Asp Pro Xaa Phe Pro Gln Thr Cys Ser Val Glu
            180                 185                 190

Ile Phe Pro Ser Pro Cys Leu Ser Xaa Thr Ile Asn Ile Xaa Ile Pro
        195                 200                 205

Leu Pro Lys Leu Ala Gly Ala Leu Xaa Leu Val Asn Pro Leu Gly Pro
    210                 215                 220

Leu
225


<210> SEQ ID NO 29
<211> LENGTH: 215
<212> TYPE: PRT
<213> ORGANISM: Homo Sapien
<220> FEATURE:
<221> NAME/KEY: VARIANT
<222> LOCATION: 1, 166, 172, 175, 192, 196, 208
<223> OTHER INFORMATION: Xaa = Any Amino Acid
<220> FEATURE:
<221> NAME/KEY: VARIANT
<222> LOCATION: 1, 166, 172, 175, 192, 196, 208
<223> OTHER INFORMATION: Xaa = Any Amino Acid

<400> SEQUENCE: 29

Xaa Ile Gln Ala Arg Gln Gly Lys Glu Glu Gly Gly Gly Arg Gln Arg
 1               5                  10                  15

Ser Ser Leu Trp Pro Ser Glu Leu Gln Lys Asp Arg Gly Pro Ser Ala
            20                  25                  30

Ala Leu Glu Ala Asp Gln Gly Cys His Ala Ala Gln Pro Gly His His
        35                  40                  45

Leu Val Ala Ala Ala Asp Thr Ser Asp Gly Trp Gln Phe Trp Ser Gly
    50                  55                  60

Cys Pro Gly Glu Gly Val Ala Asp Asp Gln Pro Pro His Gln Ala Arg
65                  70                  75                  80

Arg Leu Pro His Ser Asn Leu Val Phe Leu Ala Trp Cys Ser Asp Ser
                85                  90                  95

Ser Gln Ala Ala Pro Cys Gly Leu Ser Ala Ala Gly Ala Arg Ala Gly
            100                 105                 110

Gly Arg Val Pro Gly His Pro Ala Asp Gly His Gly Asp Pro Gln Cys
        115                 120                 125

Leu Cys Cys Val Ile His His Pro Glu Glu Leu Arg Glu Ala Gln Glu
    130                 135                 140

Ala Gln Gly Arg Asn Lys Gly Asn Asp Leu Leu Arg Ala Leu Ser Pro
145                 150                 155                 160

Ile Leu Val Gln Gln Xaa Pro Ser Cys Phe Leu Xaa Gly Thr Xaa Ile
                165                 170                 175

Phe Pro Lys Leu Ala Leu Leu Arg Phe Phe Pro His Leu Ala Ser Xaa
            180                 185                 190

Ala Gln Ile Xaa Leu Tyr His Cys Gln Ser Leu Arg Ala His Ser Xaa
        195                 200                 205

Asn Leu Thr Pro Trp Gly Leu
    210                 215


<210> SEQ ID NO 30
<211> LENGTH: 232
<212> TYPE: PRT
<213> ORGANISM: Homo Sapien
<220> FEATURE:
<221> NAME/KEY: VARIANT
<222> LOCATION: 182, 187, 191, 207, 212, 224
<223> OTHER INFORMATION: Xaa = Any Amino Acid
```

<220> FEATURE:
<221> NAME/KEY: VARIANT
<222> LOCATION: 182, 187, 191, 207, 212, 224
<223> OTHER INFORMATION: Xaa = Any Amino Acid

<400> SEQUENCE: 30

```
Glu Phe Lys Gln Asp Lys Asp Glu Lys Lys Lys Gly Glu Asp Glu Asp
 1              5                   10                  15

Lys Gly Pro Pro Cys Gly Pro Val Asn Cys Asn Glu Lys Ile Val Val
            20                  25                  30

Leu Leu Gln Arg Leu Lys Pro Glu Ile Lys Asp Val Ile Glu Gln Leu
        35                  40                  45

Asn Leu Val Thr Thr Trp Leu Gln Leu Gln Ile Pro Arg Ile Glu Asp
    50                  55                  60

Gly Asn Asn Phe Gly Val Ala Val Gln Glu Lys Val Phe Glu Leu Met
65                  70                  75                  80

Thr Ser Leu His Thr Lys Leu Glu Gly Phe His Thr Gln Ile Ser Lys
                85                  90                  95

Tyr Phe Ser Glu Arg Gly Asp Ala Val Thr Lys Ala Ala Lys Gln Pro
            100                 105                 110

His Val Gly Asp Tyr Arg Gln Leu Val His Glu Leu Asp Glu Ala Glu
        115                 120                 125

Tyr Arg Asp Ile Arg Leu Met Val Met Glu Ile Arg Asn Ala Tyr Ala
    130                 135                 140

Val Leu Tyr Asp Ile Ile Leu Lys Asn Phe Glu Lys Leu Lys Lys Pro
145                 150                 155                 160

Arg Gly Glu Thr Lys Gly Met Ile Tyr Glu Pro Ser Leu Pro Phe Cys
                165                 170                 175

Asp Glu Tyr Ser Arg Xaa Leu Pro Ala Phe Xaa Trp Gly Pro Xaa Phe
            180                 185                 190

Ser Pro Asn Leu Leu Cys Asp Phe Ser Leu Thr Leu Pro Leu Xaa His
        195                 200                 205

Asn Lys Tyr Xaa Tyr Thr Thr Ala Lys Ala Cys Gly Arg Thr Pro Xaa
    210                 215                 220

Thr Ser Pro Leu Gly Ala Ser Lys
225                 230
```

<210> SEQ ID NO 31
<211> LENGTH: 214
<212> TYPE: PRT
<213> ORGANISM: Homo Sapien
<220> FEATURE:
<221> NAME/KEY: VARIANT
<222> LOCATION: 1, 145, 149, 163, 166, 167, 170, 173, 176, 179, 180, 181, 182, 183, 185, 187, 188, 189, 192, 200, 202, 204, 205, 206, 207, 210, 212, 214
<223> OTHER INFORMATION: Xaa = Any Amino Acid
<220> FEATURE:
<221> NAME/KEY: VARIANT
<222> LOCATION: 1, 145, 149, 163, 166, 167, 170, 173, 176, 179, 180, 181, 182, 183, 185, 187, 188, 189, 192, 200, 202, 204, 205, 206, 207, 210, 212, 214
<223> OTHER INFORMATION: Xaa = Any Amino Acid

<400> SEQUENCE: 31

```
Xaa Asn Ser Gln Asn Ser Ser Glu Lys Ser Cys Phe Lys Val Leu Thr
 1              5                   10                  15

Phe Phe Gln Met Arg Lys Lys Trp Arg Lys Glu Lys Gly Asn Lys Lys
            20                  25                  30

Tyr Ser Lys Leu Ser Lys Lys Ile Asn Ser Val Lys Asn Gly Ile Ser
        35                  40                  45
```

```
Leu Pro Gly Thr Ser Phe Leu Ile Ile Gly Leu Ser Trp Gly Lys Leu
    50                  55                  60

Gly Pro Cys Leu Thr Gly Arg Phe Ser Arg Ser Cys Gly Pro Gly Glu
65                  70                  75                  80

Thr Thr Gln Asp Ser Arg Ser Trp Ser Gly Arg Leu Lys Pro Trp Lys
                85                  90                  95

Met Ile Leu Gly Lys Lys Thr Glu Asn Asn Asn Trp Pro Leu Ser Ile
            100                 105                 110

Thr Gly Asn Lys Phe Ser Asp Thr Ala Leu Gln Asn Gly Ser Ile Gly
        115                 120                 125

Met Ala Pro Ser Ser Arg Glu Ser Trp Leu Ser Gln Lys Arg Lys Leu
    130                 135                 140

Xaa Arg Arg Trp Xaa His Cys Cys Arg Gln His His Trp Gly Asn Ser
145                 150                 155                 160

Val Pro Xaa Gly Tyr Xaa Xaa Ser Val Xaa Leu Arg Xaa Glu Gln Xaa
                165                 170                 175

Trp Trp Xaa Xaa Xaa Xaa Xaa Met Xaa Arg Xaa Xaa Xaa Cys Pro Xaa
            180                 185                 190

Leu Trp Glu Lys Pro Pro Leu Xaa Ser Xaa Gly Xaa Xaa Xaa Xaa Pro
        195                 200                 205

Pro Xaa Glu Xaa Gln Xaa
    210
```

<210> SEQ ID NO 32
<211> LENGTH: 209
<212> TYPE: PRT
<213> ORGANISM: Homo Sapien
<220> FEATURE:
<221> NAME/KEY: VARIANT
<222> LOCATION: 1, 141, 145, 159, 163, 164, 166, 169, 172, 175, 176, 177, 178, 179, 181, 183, 184, 185, 188, 196, 198, 200, 201, 202, 205, 208, 209
<223> OTHER INFORMATION: Xaa = Any Amino Acid
<220> FEATURE:
<221> NAME/KEY: VARIANT
<222> LOCATION: 1, 141, 145, 159, 163, 164, 166, 169, 172, 175, 176, 177, 178, 179, 181, 183, 184, 185, 188, 196, 198, 200, 201, 202, 205, 208, 209
<223> OTHER INFORMATION: Xaa = Any Amino Acid

<400> SEQUENCE: 32

```
Xaa Ile Leu Lys Ile Val Gln Lys Asn His Val Ser Lys Tyr Ser His
 1               5                  10                  15

Ser Ser Arg Gly Lys Asn Gly Glu Gly Lys Lys Lys Glu Ile Glu Arg
            20                  25                  30

Ser Ile Asn Pro Asn Phe Gln Arg Lys Ser Thr Val Ser Lys Thr Val
        35                  40                  45

Phe Arg Cys Leu Ala Gln Ala Asp Ser Ser Asp Ala Gly Glu Ser Trp
    50                  55                  60

Asp Pro Val Leu Glu Asp Ser Ala Glu Gly Pro Ala Gly Leu Glu Arg
65                  70                  75                  80

Leu His Lys Ile Pro Glu Val Gly Ala Gly Asp Ser Ser Leu Gly Lys
                85                  90                  95

Ser Gly Arg Lys Gln Lys Thr Thr Thr Gly His Val Pro Glu Thr Ser
            100                 105                 110

Ser Pro Thr Leu Leu Tyr Arg Met Ala Ala Leu Ala Trp Arg Arg Ala
        115                 120                 125

Pro Glu Glu Arg Ala Gly Ser His Lys Arg Gly Asn Xaa Glu Glu Asp
    130                 135                 140
```

-continued

```
Xaa Cys Thr Ala Ala Gly Ser Ile Thr Gly Glu Thr Gln Cys Xaa Trp
145                 150                 155                 160

Val Ile Xaa Xaa Gln Xaa Thr Gly Xaa Asn Ser Xaa Gly Gly Xaa Xaa
                165                 170                 175

Xaa Xaa Xaa Trp Xaa Gly Xaa Xaa Xaa Ala Pro Xaa Cys Gly Lys Ser
            180                 185                 190

Pro Pro Trp Xaa Ala Xaa Gly Xaa Xaa Xaa Ser Pro Xaa Gly Lys Xaa
        195                 200                 205

Xaa


<210> SEQ ID NO 33
<211> LENGTH: 218
<212> TYPE: PRT
<213> ORGANISM: Homo Sapien
<220> FEATURE:
<221> NAME/KEY: VARIANT
<222> LOCATION: 149, 153, 167, 171, 172, 174, 177, 181, 184, 186, 187,
      189, 191, 192, 193, 194, 196, 205, 206, 209, 210, 211, 214, 216,
      218
<223> OTHER INFORMATION: Xaa = Any Amino Acid
<220> FEATURE:
<221> NAME/KEY: VARIANT
<222> LOCATION: 149, 153, 167, 171, 172, 174, 177, 181, 184, 186, 187,
      189, 191, 192, 193, 194, 196, 205, 206, 209, 210, 211, 214, 216,
      218
<223> OTHER INFORMATION: Xaa = Any Amino Acid

<400> SEQUENCE: 33

Glu Phe Ser Lys Phe Arg Lys Ile Met Phe Gln Ser Thr His Ile Leu
 1               5                  10                  15

Pro Asp Glu Glu Lys Met Val Lys Glu Arg Lys Arg Lys Leu Lys Glu
            20                  25                  30

Val Leu Ile Gln Thr Phe Lys Glu Asn Gln Gln Cys Gln Lys Arg Tyr
        35                  40                  45

Phe Ala Ala Trp His Lys Leu Ile Leu Asp His Arg Ile Lys Leu Gly
    50                  55                  60

Lys Ala Gly Thr Leu Ser Asp Trp Lys Ile Gln Leu Lys Val Leu Arg
65                  70                  75                  80

Ala Trp Arg Asp Tyr Thr Arg Phe Gln Lys Leu Glu Arg Glu Thr Gln
                85                  90                  95

Ala Leu Glu Asn Asp Leu Arg Glu Glu Asn Arg Lys Gln Gln Leu Ala
            100                 105                 110

Thr Glu Tyr Asn Arg Lys Gln Val Leu Arg His Cys Phe Thr Glu Trp
        115                 120                 125

Gln His Trp His Gly Ala Glu Leu Leu Lys Arg Glu Leu Ala Leu Thr
    130                 135                 140

Lys Glu Glu Thr Xaa Lys Lys Met Xaa Ala Leu Leu Gln Ala Ala Ser
145                 150                 155                 160

Leu Gly Lys Leu Ser Ala Xaa Gly Leu Ser Xaa Xaa Ser Xaa Pro Glu
                165                 170                 175

Xaa Gly Thr Ala Xaa Val Gly Xaa Pro Xaa Xaa Asn Xaa Gln Xaa Xaa
            180                 185                 190

Xaa Xaa Pro Xaa Phe Val Gly Lys Ala Pro Leu Gly Xaa Xaa Trp Val
        195                 200                 205

Xaa Xaa Xaa Pro Pro Xaa Gly Xaa Thr Xaa
    210                 215


<210> SEQ ID NO 34
<211> LENGTH: 135
```

<212> TYPE: PRT
<213> ORGANISM: Homo Sapien
<220> FEATURE:
<221> NAME/KEY: VARIANT
<222> LOCATION: 1, 69, 135
<223> OTHER INFORMATION: Xaa = Any Amino Acid
<220> FEATURE:
<221> NAME/KEY: VARIANT
<222> LOCATION: 1, 69, 135
<223> OTHER INFORMATION: Xaa = Any Amino Acid

<400> SEQUENCE: 34

```
Xaa Asn Ser Gly Lys Leu Gly Thr Thr Val Lys Pro Lys Ser Leu Val
 1               5                  10                  15

Thr Ser Ser Ser Gly Ala Leu Lys Lys Gln His Lys Lys Pro Phe Asp
            20                  25                  30

Ala Met Asn Asn Ile Val Ala Asn Leu Leu Leu Asn Leu Thr Arg Glu
        35                  40                  45

Ala Cys Gly Arg Thr Arg Val Thr Ser Pro Leu Gly Ala Ser Lys Arg
    50                  55                  60

Val Leu Arg Gly Xaa Leu Ser Tyr Ser Ser Ala Ala Ala Ser Phe Pro
65                  70                  75                  80

Arg Val Glu Glu Gln Ile Cys His Asn Val Ile His Cys Ile Lys Gly
                85                  90                  95

Leu Leu Met Leu Leu Phe Ser Pro Arg Thr Ser Asn Gln Thr Leu Trp
            100                 105                 110

Leu His Ser Cys Thr Gln Leu Ser Arg Ile Arg Ile Pro Glu His His
        115                 120                 125

Thr Leu Glu Tyr Asp Ser Xaa
    130                 135
```

<210> SEQ ID NO 35
<211> LENGTH: 133
<212> TYPE: PRT
<213> ORGANISM: Homo Sapien
<220> FEATURE:
<221> NAME/KEY: VARIANT
<222> LOCATION: 1, 63, 133
<223> OTHER INFORMATION: Xaa = Any Amino Acid
<220> FEATURE:
<221> NAME/KEY: VARIANT
<222> LOCATION: 1, 63, 133
<223> OTHER INFORMATION: Xaa = Any Amino Acid

<400> SEQUENCE: 35

```
Xaa Ile Leu Glu Ser Trp Val Gln Leu Ser Gln Arg Val Trp Leu Leu
 1               5                  10                  15

Gln Val Leu Gly Leu Lys Ser Ser Ile Arg Ser Pro Leu Met Gln Ile
            20                  25                  30

Thr Leu Trp Gln Ile Cys Ser Ser Thr Arg Gly Lys Leu Ala Ala Ala
        35                  40                  45

Leu Glu Leu Val Asn Pro Leu Gly Pro Leu Asn Gly Ser Gly Xaa Tyr
    50                  55                  60

Val Thr Arg Val Arg Pro Gln Ala Ser Leu Val Arg Leu Arg Ser Lys
65                  70                  75                  80

Phe Ala Thr Met Leu Phe Ile Ala Ser Lys Gly Phe Leu Cys Cys Phe
                85                  90                  95

Phe Lys Ala Pro Glu Leu Glu Val Thr Arg Leu Phe Gly Phe Thr Val
            100                 105                 110

Val Pro Asn Phe Pro Glu Phe Gly Ser Pro Ser Ile Thr Pro Asp Trp
        115                 120                 125
```

-continued

```
Asn Thr Thr Ala Xaa
    130


<210> SEQ ID NO 36
<211> LENGTH: 133
<212> TYPE: PRT
<213> ORGANISM: Homo Sapien
<220> FEATURE:
<221> NAME/KEY: VARIANT
<222> LOCATION: 64, 132
<223> OTHER INFORMATION: Xaa = Any Amino Acid
<220> FEATURE:
<221> NAME/KEY: VARIANT
<222> LOCATION: 64, 132
<223> OTHER INFORMATION: Xaa = Any Amino Acid

<400> SEQUENCE: 36

Glu Phe Trp Lys Val Gly Tyr Asn Cys Glu Ala Lys Glu Ser Gly Tyr
 1               5                  10                  15

Phe Lys Phe Trp Gly Phe Lys Lys Ala Ala Glu Ala Leu Cys Asn Glu
            20                  25                  30

His Cys Gly Lys Phe Ala Pro Gln Pro Asn Glu Gly Ser Leu Arg Pro
        35                  40                  45

His Ser Ser Asn Leu Thr Pro Trp Gly Leu Thr Gly Leu Glu Gly Xaa
    50                  55                  60

Thr Lys Leu Leu Glu Cys Gly Arg Lys Leu Pro Ser Leu Gly Gly Ala
65                  70                  75                  80

Asn Leu Pro Gln Cys Tyr Ser Leu His Gln Arg Ala Ser Tyr Ala Ala
                85                  90                  95

Phe Leu Lys Pro Gln Asn Leu Lys Pro Asp Ser Leu Ala Ser Gln Leu
            100                 105                 110

Tyr Pro Thr Phe Gln Asn Ser Asp Pro Arg Ala Ser His Leu Thr Gly
        115                 120                 125

Ile Arg Gln Xaa Gln
    130
```

METHOD FOR IDENTIFYING TARGETING DOMAINS AND METHODS AND COMPOSITIONS COMPRISING THE SAME

STATEMENT REGARDING FEDERALLY SPONSORED RESEARCH FOR DEVELOPMENT

This invention was made with government support under National Institutes of Health (NIH)SPORE Grant No. CA58185 and NIH Grant No. K04, and the United States Government may have certain rights in the invention.

CROSS-REFERENCE TO RELATED APPLICATIONS

This application claims the benefit of U.S. Provisional Application Ser. No. 60/345,520, filed Feb. 8, 2002, the disclosure of which is incorporated herein by reference in its entirety.

FIELD OF THE INVENTION

The present invention relates to the identification of tissue targeting domains. In particular, the invention relates to methods for identifying a polynucleotide encoding a targeting domain which directs tumor cell localization to secondary sites, to methods of utilizing the polynucleotide and corresponding polypeptide or fragments thereof and compositions comprising the same.

BACKGROUND OF THE INVENTION

Cancer is a leading cause of death in the United States. In 2001, of the over half a million deaths in the United States, one in every four deaths was likely attributable to cancer. If all cancers were diagnosed at a localized stage, the five year survival rate would be over 95%. Overall, metastasis is considered by many to be the deadliest aspect of cancer.

It has been clinically noted that particular primary tumors tend to metastasize to specific distant organs. For example, prostate cancer often metastasizes to the bone, breast cancer may metastasize to the liver, melanomas tend to spread to lymph nodes, ovarian cancer metastasizes to other areas of the body including the lungs, brain, lymph and bones. Once a cancer has spread, it becomes much more lethal. No longer is a simple surgical intervention (e.g., to remove the primary tumor) an effective form of treatment. In addition, "blunt instruments" (e.g., radiation treatment and chemotherapy) affect not only cancerous cells, but also normal tissues throughout the body.

Cancer metastasis involves a series of sequential steps. After the initial transforming event, growth of neoplastic cells must be progressive. Extensive vascularization or angiogeneis also must occur, which allows blood vessels to grow into the tumor mass, bringing nourishment and allowing increased tumor growth. As the vascularization increases and the tumor grows, the thin walled venules or anastomoses of the capillary network allow for the penetration of cancer cells. These cells then may detach from the tumor mass and enter the circulation in a process called "embolization." The majority of cancer cell aggregates that enter the circulation is destroyed, yet some of the aggregates migrate to distant capillary beds and begin a process called extravasation. During extravasation, tumor cells exit the capillary network, colonize a distant organ and create a secondary or metastatic tumor. This "homing," or metastasis, of particular types of tumor cells to specific "target" organs provides further evidence that organ-specific markers exist.

The extravasation process is thought to begin with a type of adherence to the vascular walls—either by (i) attachment to specific proteins on the endothelial surface of the vasculature or (ii) a non-specific type of adhesion to the homing molecule at the target organ. In either case, there exists the possibility for multiple molecules and mechanisms of adherence of both homing molecules from primary tumors of different origins and for target molecules at the site of secondary metastatic tumors in specific organs.

Dreyer and Hood formulated the "Area Code Hypothesis" in the study of embryology and tissue differentiation. *J. Supramol Struct.* 1977;7(3-4);531-559. This hypothesis is concerned with the structure, function and regulation of cell-surface molecules that mediate recognition during embryogenesis. Ruoslahti and Pasqualini, who applied the area code hypothesis, developed a method that involved putting random peptide sequences in a phage display library, which then were injected into mice (see e.g. U.S. Pat. Nos. 5,622,699 and 6,232,287). Such "in vivo phage display" led to the identification of several molecular motifs, which localized to specific organs. The goal which Ruoslahti and Pasqualini hoped to achieve was a method to specifically attack metastatic tumors using the identified motifs. However, the physiologic basis for this targeting remains unknown, and neither the native homing molecules on the metastatic cell or the target molecule at the site of the secondary tumor have been identified, with singular exceptions.

In addition, Pasqualini and Ruoslahti expressed skepticism that organs, which filter a high blood volume would be amenable to the procedure they described, due to their ability to non-specifically capture a large number of blood borne peptides. Nevertheless, the clinical observation that particular primary tumors do home in on target organs in spite of their small volume of blood flow, prior to colonizing organs with high volumes, such as the liver, kidney or lungs is well documented. If these mechanisms could be identified, powerful new ways to study and treat cancer would be available. There is, therefore, a well recognized need to identify molecules that allow the homing of cancer cells in vivo. In the same vein, there is a need for a mechanism to identify molecules at distant sites that are targeted by metastasizing cells.

SUMMARY OF THE INVENTION

The present invention overcomes the problems and disadvantages associated with current strategies and designs and provides new diagnostic and therapeutic methods relating to metastatic disease. The invention relates generally to a method of identifying a polynucleotide encoding a targeting domain which directs tumor cell localization to secondary site (e.g., metastasis), to the isolated polynucleotide and/or corresponding polypetide identified by the method, to methods of utilizing the polynucleotide and/or corresponding polypeptide in diagnostic and therapeutic applications and to compositions comprising the same.

One aspect of the invention provides a method of identifying a polynucleotide encoding a targeting domain associated with metastasis of tumor cells, the method comprising: (a) administering a phage displaying libraries comprising a collection of phages containing polynucleotides from, preferably, a primary tumor cell into a subject; (b) selecting phage that localize in a target organ or tissue; (c) collecting phage from the selected organ or tissue; (d) repeating steps (a) and (c) for one or more cycles; and (e) identifying one or more polynucleotides encoding a targeting domain or fragment thereof from selected phage that are associated with tumor cell metastasis. This method allows for the identification of polynucleotides and their expression products that are associated with metastasis and, preferably, those responsible for metastatic disease or organ targeting.

In one embodiment of the method, cDNA libraries from different primary tumors are packaged into T7 phage and injected in vivo into mice. After circulation, organs are extracted, a phage titer determined, and phage amplified in bacterial cells. This process of injection, organ removal and rescue and amplification of phage from the target organ (i.e. biopanning), is repeated multiple times and results in enrichment for phage possessing organ selectivity when compared to empty plasmid controls. The polynucleotide and/or expression product (e.g., polypeptide) of the phage exhibiting organ selectivity are characterized by well-known biochemical methods.

Another aspect of this invention is directed to isolated polynucleotides identified by the method described herein. In one embodiment, the polynucleotide hybridizes under stringent conditions to a polynucleotide comprising the sequence of SEQ ID NOS: 1, 2, 3, 4, 5, 6, 7, 8, or 9. In another embodiment, the polynucleotide comprises the sequence of SEQ ID NOS: 1, 2, 3, 4, 5, 6, 7, 8 or 9. In yet another embodiment the isolated polynucleotide encodes a polypeptide comprising the polypeptide sequence of SEQ ID NOS: 10, 11, 12, 13, 14, 15, 16, 17, 18, 19, 20, 21, 22, 23, 24, 25, 26, 27, 28, 29, 30, 31, 32, 33, 34, 35, or 36. In yet another embodiment, the polynucleotide encodes a polypeptide comprising a targeting domain of the polypeptide of SEQ ID NOS: 10, 11, 12, 13, 14, 15, 16, 17, 18, 19, 20, 21, 22, 23, 24, 25, 26, 27, 28, 29, 30, 31, 32, 33, 34, 35, or 36.

Another aspect of this invention is directed to isolated polypeptides identified by the method described herein. In one embodiment the polypeptide comprises the amino acid sequence of SEQ ID. NOS: 10, 11, 12, 13, 14, 15, 16, 17, 18, 19, 20, 21, 22, 23, 24, 25, 26, 27, 28, 29, 30, 31, 32, 33, 34, 35, or 36.

In yet another aspect of the invention, microarrays comprising the polynucleotides and/or polypeptides of the invention are provided.

Yet another aspect of the inventions relates to an antibody directed against the polypeptides of the invention.

In yet another aspect, polypeptides comprising the targeting domain coupled to a moiety (e.g., therapeutic or detection moiety) are provided.

Yet another aspect of this invention provides methods of prognosing and/or diagnosing metastatic disease in a subject. In one embodiment, the method comprises detecting the level of a polynucleotide encoding a polypeptide comprising the targeting domain in a sample obtained from a subject, wherein a higher level of the polynucleotide relative to a control sample (e.g., population controls or non-metastaic control sample) is indicative of metastatic disease. In another embodiment, the method comprises detecting the presence or absence of a polynucleotide encoding a polypeptide comprising the targeting domain in a sample obtained from the subject, wherein the presence of the polynucleotide is indicative of metastatic disease.

Yet another aspect of this invention provides methods of prognosing and/or diagnosing metastatic disease in a subject. In one embodiment, the method comprises detecting the level of a polypeptide comprising the targeting domain in a sample obtained from a subject, wherein a higher level of the polypeptide relative to a control sample (e.g., population controls or non-metastaic control sample) is indicative of metastatic disease. In another embodiment, the method comprises detecting the presence or absence of a polypeptide comprising a targeting domain in a sample obtained from the subject, wherein the presence of the polypeptide is indicative of metastatic disease.

Yet another aspect of the invention relates to detection of metastatic disease in a subject, such as a human utilizing antibodies coupled to a radiologic or other imaging molecules to detect metastisis in the subject.

A further aspect of the invention comprises methods of treating metastasis in a subject in need of such treatment. In some embodiments the method comprises administering to a subject in need of such treatment a targeting domain linked to a therapeutic agent in an amount effective to treat the metastasis, or an effective amount of a composition that inhibits the metastasis (e.g., collection of phage or phage expression products identified by the method herein; a targeting domain linked to a therapeutic agent and/or an antibody directed against a polypeptide comprising a targeting domain).

Yet another aspect of the invention provides methods of screening for candidate agents that inhibit the selectivity of the targeting domain.

Yet another aspect of the invention relates to kits and compositions for use in the methods described herein.

Other embodiments and advantages of the invention are set forth in part in the description, which follows, and in part, may be obvious from this description, or may be learned from the practice of the invention.

DESCRIPTION OF THE FIGURES

FIG. 4: shows the clone ID, frequency of clones in percent, and peptide insert length from the liver-selected library after the final round (four rounds total) of biopanning.

FIG. 6: (A-C) shows the polynucleotide sequences for SEQ ID NOs: 1-9.

FIG. 7: (A-E) shows the polypeptide sequences for SEQ ID NOs: 10-36.

FIG. 8: is a comparison of patient cases with and without known metastasis indicating a highly significant increases in expression levels and frequency of the phage-display derived metastasis genes and of PTN for the cases with metastasis.

DETAILED DESCRIPTION OF THE INVENTION

Figure 1:
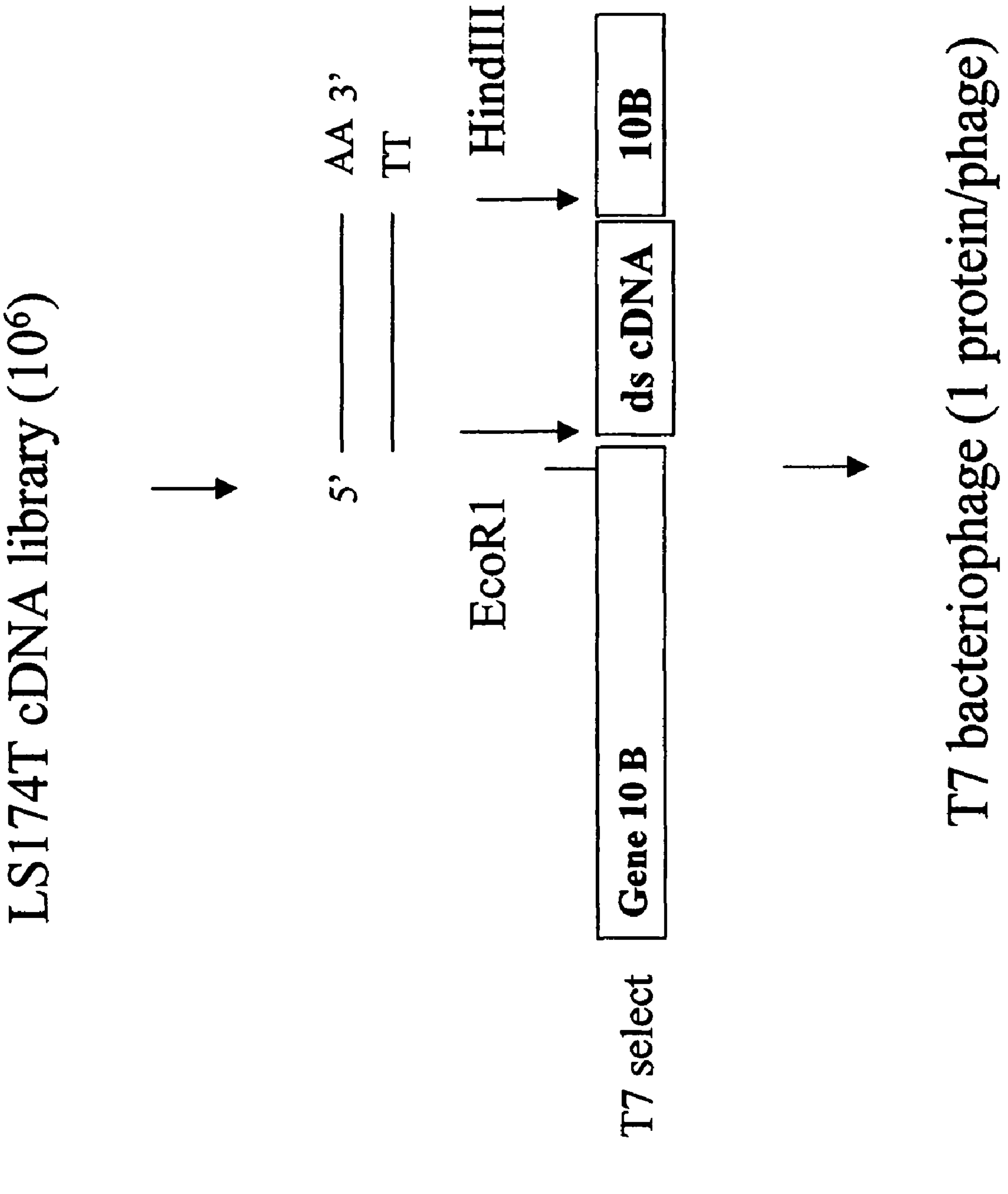
FIG. 1: is a diagrammatic representation of the preparation of the LS174T library showing the directional cloning of tumor cDNA into the T7 expression vector. cDNA, digested with EcoR1 and HindIII produced cDNA with and EcoR1 5' and HindIII 3' end. Ligation of these fragments into the T7 vector was through the corresponding EcoR1/HindIII vector arms so that inserts were in the sense orientation relative to the upstream expression signal.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Definitions

As used herein, the singular form "a", "an", and "the" includes plural references unless indicated otherwise. For example, "a" polynucleotide includes one or more polynucleotides and "a targeting domain" means one or more targeting domains.

The term "targeting domain" or "homing domain" or "homing molecule" or "homing protein" generally, but not exclusively, refers to a polypeptide that selectively or preferentially targets a particular cell type and/or tissue. By way of example, a targeting domain directs tumor cell localization from a primary tumor (e.g., colon cancer) to secondary sites (e.g., liver, lung, marrow and/or lung).

The term "selectively targets" or "preferentially targets" (used interchangeably herein) is a term well understood in the art, and methods to determine such specific or preferential targeting are also well known in the art. A polypeptide is said to exhibit "selective" or "preferential" targeting if it reacts or associates more frequently, more rapidly, with greater duration and/or with greater affinity with a particular cell and/or tissue than it does with alternative cells and/or tissues. "Selectively targets" or "preferentially targets" does not necessarily require (although it can include) exclusive binding. By way of example, a polypeptide identified by the methods described herein selectively or preferentially targets a cell or tissue if it exhibits between about 3 to about 300 fold selectivity. Method for determining selective or preferential targeting are exemplified herein.

An "subject" may be any animal, preferably a vertebrate, most preferably a mammal. Examples, include, but are not limited to, rodents (e.g., mouse or rats), cats, dogs, rabbits, farm animals (e.g., pigs, horses, cows) or humans.

As embodied and broadly described herein, the present invention is directed to novel methods of identifying polynucleotides encoding targeting domains associated with metastatisis disease or disorders, the polynucleotides and polypeptides identified by the method. The invention is also directed to diagnostic and therapeutic compositions, kits and methods useful in the treatment, prevent and detection of metastatic disorders.

Method of Identifying Targeting Domains

The ability of tumors to metastasize is, at least in part, the result of genes whose products comprise a targeting domain which selectively directs a tumor cell from the primary tumor to secondary tissue metastatic sites. By way of example, the targeting domain may act as a receptor to a ligand on the surface of vessels in the specific target organs or as ligands to receptor proteins on the surface of vessels in those organs. This invention is based on the discovery of a method which identifies polynucleotides associated with metastasis and the targeting domain encoded by such polynucleotides. These polynucleotides and/or polypeptides, provide an understanding of the mechanism of action of metastatic tumors at a molecular level.

One embodiment of the invention is directed to libraries created from primary tumors that can be utilized for the identification of homing genes. As different homing proteins may have different targets in different tissues, another embodiment of the invention to directed to methods for identifying targeting molecules from different primary tissue types and their complimentary targets from different sites of metastasis.

Genes responsible for metastatic targeting of one or more organs, tissues and other areas of the body, can be identified by the current invention. Primary tumors that are known to metastasize to particular organs are selected for the production of a phage library. That library is then injected into an appropriate model. The model is preferably a mammal such as, for example, a human, a mouse or a rabbit, but may also be any other mammal. Alternatively, the method may utilize any animal, including non-mammals, that allows for the injection of phage library and demonstrates a significant response.

Human tumor libraries are often not available or may not yield the greatest response in a non-human model. Accordingly, the present invention comprises tumor libraries derived from animals that show a response in the model. With the successful completion of the human genome project, identification of homing and target genes in a non-human library for the identification of human homologues.

Accordingly, this invention provides a method of identifying a polynucleotide encoding a targeting domain associated with metastasis of tumor cells, the method comprising: (a) administering a phage displaying libraries comprising a collection of phages containing polynucleotides from a primary tumor cell into a subject; (b) selecting phage that localize in a target organ or tissue; (c) collecting phage from the selected organ or tissue; (d) repeating steps (a) and (c) for one or more cycles; and (e) identifying one or more polynucleotides encoding a targeting domain or fragment thereof from selected phage that are associated with tumor cell metastasis.

Any library may be used in the method described herein. Standard methods may be utilized to create the library or the library may be obtained from a commercial source. Examples of libraries that may be used in the method include, but are not limited to libraries created from primary tumors of lung, stomach, colon, rectum, prostate, pancreas, liver, leukemia, breast, uterus, ovary, melanoma, urinary tract, bladder, cervix, lymph, brain, nervous system or combinations thereof, peptide libraries, or libraries comprising molecules sharing common functional domains or sequence (e.g., kinases, cytokines, growth factors etc) or polynucleotides from any eukaryarotic cell. In one embodiment, a library used in the method is reused with the clones isolated from the first screen subtracted out from the library to minimize repetitive isolation of the same clone. Methods of creating subtraction libraries are well known in the art.

Any phage may be used to create the library. Preferably, the phage used in the creation of the library has one or more of the following characteristics: the ability to contain and relatively large polynucleotides, such as, for example, between about 300-3000 nucleotides and/or expresses the clone from the library at a low copy numbers, such as, for example, between about 0.1 copy to about 1 copy per phage. Such phage are commercially available (e.g., a T7Select vector using T7Select 1-1 phage). By way of example, a phage display library may comprise and express polynucleotides isolated from a primary tumor, such as, for example, colon cancer or from a cell line such as, for example, a colon cancer cell line (e.g., LS174T; American tissue culture collection, ATCC, Rockville, Md.). Preferably, the phage themselves (i.e. phage without a recombinant insert) have a low relative retention to target organs or cells. Retention, which may relate to direct binding, non-specific association, or active uptake, will cause phage to nonspecifically associate with target cells. By identifying and selecting only phage with low retentions by target cells, the highest selectivity can be achieved. Relative retention of phage to target tissue is preferably less than 50%, more preferably less than 10%, and still more preferably less than 1%.

The library is administered to any subject, preferably a mouse or other mammal. The animal may be a normal animal or an animal model of disease. Alternatively, the library may be contacted with in vitro systems or models. In an animal, such as for example, a mouse, a volume of between about 10 microliters to about 100 microliters containing between about $10^7$ to about $10^{10}$ phage is administered to a mouse. Phage, based on the expression product displayed, target to selected organs, tissues or other areas of the body. Accordingly, the library is administered and allowed to circulate for a time to sufficient to allow binding to the target tissue and/or organ of the binding domains expressed in the library. The optimal circulation time will vary with the size/weight of the animal, volume and/or complexity of the library. By way of example, for a mouse circulation time may be preferably between about one minute to about ten minutes.

After sufficient circulation time the animal is euthanized and the target organs collected for analysis. The method described herein may be further enhanced by further comprising perfusing the anesthetized animal with an isotonic salt solution with or without proteins (e.g., BSA) to minimize non-specific binding of phage. Examples of isotonic salt solutions include, but are not limited to phosphate buffer. Perfusion is continued, preferably until desanguination (e.g., little or no blood exits the vena cava, organs appear white in color.) By way of example, volumes of between about 1 to about 100, preferably about 20 times the volume of the animal may be used.

Any organ or tissue may be harvested for analysis. By way of example, but not limited to bone marrow, lung, skin, liver and/or brain. Generally the tissue or organ harvested will be selected based on the origin of the library. By way of example, metastisis in colon cancer is often to the liver, marrow, lung and/or bone marrow. If the library used in the method comprised polynucleotides from a primary colon cancer tumor or cell line, liver lung and/or bone marrow can be harvested Phage are collected from the selected tissues and/or organs, amplified, if necessary, and injected into another animal. Through successive rounds of injection, selection, and amplification, a collection of phage can be isolated that are specific for the selection criteria. By way of example, between about two to about five rounds of injection, selection, and amplification may performed. These collections can be further selected or the polynucleotides from individual or groups of phage isolated and identified. Polynucleotides identified by these methods can be used for both diagnostic and therapeutic purposes. The polynucleotide expression products identified may be useful to distinguish metastatic from non-metastatic disease. Alternatively, the products may be useful in identifying new therapies for the treatment of metastatic and for the screening of promising pharmaceutical products.

The method described herein for identifying targeting domains may also be utilized to identify targeting domains in other diseases or disorders. By way of example, such diseases or disorders may include, but are not limited to, arteriosclerosis, coronary artery disease, stroke, diabetic vascular damage (e.g., kidney vascular damage) or retinopathy. Examples of animals models to be used in the methods described herein include, but are not limited to, cardiovascular diseases in in pig, rat, rabbit arterial stenosis and vascularization. (e.g., Goodman and Gilman's: the Pharmaceutical Basis of Therapeutics Pergamon Press (1990)).

Polynucleotides

Another aspect of this invention is directed to isolated polynucleotides identified by the method described herein. The term polynucleotide is used broadly and refers to polymeric nucleotides of any length (e.g., oligonucleotides, genes, small inhibiting RNA etc). The polynucleotide of the invention may be, for example, linear, circular, supercoiled, single stranded, double stranded or branched. The nucleotides comprising the polynucleotide may be naturally occurring nucleotides or modified nucleotides. The polynucleotides illustrated in FIGS. 6A-6B (SEQ ID NOS. 1-9) and/or their complement represent preferred embodiments of the invention. It is, however, understood by one skilled in the art that due to the degeneracy of the genetic code variations in the polynucleotide sequences shown will still result in a polynucleotide sequence capable of encoding a targeting domain. Such polynucleotide sequences are therefore functionally equivalent to the sequence set forth in FIGS. 6A-6C and are intended to be encompassed within the present invention. Further, a person of skill in the art will understand that there are naturally occurring allelic variations of the polynucleotide sequences shown in FIGS. 6A-6C these variations are also intended to be encompassed by the present invention.

In one embodiment the polynucleotide comprises the sequence of SEQ ID NOS: 1, 2, 3, 4, 5, 6, 7, 8, or 9. In yet another embodiment the isolated polynucleotide encodes a polypeptide comprising the polypeptide sequence of SEQ ID NOS: 10, 11, 12, 13, 14, 15, 16, 17, 18, 19, 20, 21, 22, 23, 24, 25, 26, 27, 28, 29, 30, 31, 32, 33, 34, 35, or 36. In another embodiment, the polynucleotide encodes a polypeptide comprising a targeting domain of the polypeptide of SEQ ID NOS: 10, 11, 12, 13, 14, 15, 16, 17, 18, 19, 20, 21, 22, 23, 24, 25, 26, 27, 28, 29, 30, 31, 32, 33, 34, 35, or 36.

This invention also relates to a polynucleotide that hybridizes under stringent conditions to a polynucleotide comprising the sequence of SEQ ID NOS: 1, 2, 3, 4, 5, 6, 7, 8, or 9. Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 4×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. In a preferred embodiment hybridization and wash conditions are done at high stringency. By way of example hybridization may be performed at 50% formamide and 4×SSC followed by washes of 2×SSC/formamide at 50° C. and with 1×SSC (see example).

Polypeptides

Another aspect of this invention is directed to isolated polypeptides identified by the methods described herein. The term polypeptide is used broadly herein to include peptide or protein or fragments thereof. Also intended to be encompassed are peptidomimetics, which include chemically modified peptides, peptide-like molecules containing normaturally occurring amino acids, peptoids and the like, have the selective binding of the targeting domains provided herein. ("Burger's Medicinal Chemistry and Drug Discovery" 5th ed., vols. 1 to 3 (ed. M. E. Wolff; Wiley Interscience 1995).

In one embodiment the polypeptide comprises the amino acid sequence of SEQ ID NOS: 10, 11, 12, 13, 14, 15, 16, 17, 18, 19, 20, 21, 22, 23, 24, 25, 26, 27, 28, 29, 30, 31, 32, 33, 34, 35, or 36. This invention further includes polypeptides or analogs thereof having substantially the same function as the polypeptides of this invention. Such polypeptides include, but are not limited to, a substitution, addition or deletion mutant of the polypeptide. This invention also encompasses proteins or peptides that are substantially homologous to the polypeptides.

The term "analog" includes any polypeptide having an amino acid residue sequence substantially identical to at least one the polypeptide sequences specifically shown herein (FIGS. 7A-7E) in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a any one of the polypeptides whose sequences is described herein.

Methods of Prognosing and/or Diagnosing

The level of metastasis may be correlated to the level of primary tumor growth leading to increased neoplastic embolism which then increases the level of neoplastic aggregates in the blood stream. A method of quantitatively measuring the RNA transcription product in the blood would allow an estimation of primary tumor growth and the metastatic potential of the tumor. In some cases, quantitative measurements can be made with a PCR or, alternatively, other methods to quantitatively measure transcription may be desirable. In many situations, different primary tumors metastasize to different organs.

The methods provided herein may be prognostic (e.g., detect subclinical metastasis, detection of subclinical metastasis in at risk patients, risk of metastasis) or diagnostic (e.g., detect metastasis, monitor disease progression or treatment). One embodiment, provides methods of prognosing and/or diagnosing metastatic disease in a subject. In one embodiment, the method comprises detecting the level of a polynucleotide encoding a polypeptide comprising the targeting domain in a sample obtained from a subject, wherein a higher level of the polynucleotide relative to a control sample (e.g., population controls or non-metastaic control sample) is indicative of metastatic disease. In another embodiment, the method comprises detecting the presence or absence of a polynucleotide encoding a polypeptide comprising the targeting domain in a sample obtained from the subject, wherein the presence of the polynucleotide is indicative of metastatic disease. Conventional methodology may be used to detect the polynucleotides in the method described herein. Examples include, but are not limited to, PCR analysis, RT-PCR, Northern analysis or microarrays as described herein below. Examples of a sample obtained from a subject include, but is not limited to, blood, biopsy sample, pathology sample, urine or cerebrospinal fluid.

Yet another aspect of this invention provides methods of prognosing, imaging and/or diagnosing metastatic disease in a subject. In one embodiment, the method comprises detecting the level of a polypeptide comprising the targeting domain in a sample obtained from a subject, wherein a higher level of the polypeptide relative to a control sample (e.g., population controls or non-metastaic control sample) is indicative of metastatic disease. In another embodiment, the method comprises detecting the presence or absence of a polypeptide comprising a targeting domain in a sample obtained from the subject, wherein the presence of the polypeptide is indicative of metastatic disease. Conventional methodology may be used to detect the polypeptides in the method described herein.

Examples include, but are not limited to, Western blot analysis or protein microarrays. Other methods of quantitative analysis of proteins include, for example, proteomics technologies such as isotope coded affinity tag reagents, MALDI TOF/TOF tandem mass spectrometry, and 2D-gel/ mass spectrometry technologies. These technologies are commercially available from, for example, Large Scale Proteomics, Inc. (Germantown, Md.) and Oxford Glycosystems (Oxford UK). Methods for quantitatively measuring proteins such as ELISA analyses are well known. Kits for measuring levels of many proteins using ELISA assays are commercially available from many suppliers. In addition, methods for developing ELISA assays in the laboratory are well known. See for example Antibodies: A Laboratory Manual (Harlow and Lane Eds. Cold Spring Harbor Press). Antibodies for use in such ELISA methods either are commercially available or are prepared using well-known methods. Examples of a sample obtained from a subject include, but is not limited to, blood, biopsy sample, pathology sample, urine or cerebrospinal fluid.

Microarrays

In yet another aspect of the invention, microarrays comprising one or more of the polynucleotides and/or one or more of the polypetides of the invention. Preferred polynucleotide sequences are shown in FIGS. 6A-6C. preferred polypeptide sequences are shown in FIGS. 7A-7C. Methods of making microarrays are known in the art. By way of example, one or more of the polynucleotide sequences described herein may comprise an array of polynucleotides attached to a support (e.g., dot blots on a nylon hybridization membrane Sambrook et al., or Ausubel et al) that is contacted with the nucleic acids isolated from, for example, a patient sample.

Microarrays may be a solid phase on the surface of which are immobilized a polpopulation of the nucleic acids of the invention. Microarrays can be generated in a number of ways. The polynucleotides can be attached to a solid support or surface, which may be made from, for example, glass, plastic (e.g., polypropylene, nylon), polyacrylamide, nitrocellulose, or other materials. Methods for attaching the nucleic acids to the surface of the solid phase include, but are not limited to, printing on glass plates (Schena et al, 1995, *Science* 270:467-470; DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286); or ink jet printer.

The microarrays can also be high-density oligonucleotide arrays. Techniques are known for producing arrays containing thousands of oligonucleotides complementary to defined sequences (see, Fodor et al., (1991) *Science* 251:767-773; Pease et al., (1994) *Proc. Natl. Acad. Sci. U.S.A.* 91:5022-5026; Lockhart et al., (1996) *Nature Biotechnology* 14:1675; U.S. Pat. Nos. 5,578,832; 5,556,752; and 5,510,270; Blanchard et al., *Biosensors & Bioelectronics* 11:687-690). Other methods for making microarrays may also be utilized (Maskos and Southern, (1992) *Nuc. Acids. Res.* 20:1679-1684; U.S. Pat. No. 6,136,592; WO 200054883; WO 200055363; WO 200053812; WO 200014273). The microarrays may be used as is or incorporated into a biochip, multiwell or other device.

Antibodies

The invention also provides antibodies which specifically bind one or more of the polypetides of the invention. The antibodies can be monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). The epitope(s) can be continuous or discontinuous. The antibodies may be made by any method known in the art and tested by the method described herein. In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; 6,265,150; and Winter et al., *Annu. Rev. Immunol.* 12:433-455 (1994). Alternatively, the phage display technology (McCafferty et al., *Nature* 348:552-553 (1990)) can be used to produce human antibodies and antibody fragments in vitro, from immunoglobulin variable (V) domain gene repertoires from unimmunized donors.

Yet another aspect of the invention relates to detection of metastatic disease in a subject, such as a human utilizing one or more antibodies described herein coupled to a radiologic (e.g., $I^{125}$) or other imaging molecules (e.g., dyes, pigments or fluorescent molecules such as luciferase, fluroscein or commercially available fluorescent molecules from quantum.com). The antibodies may be coupled to the radiologic or imaging molecule by methods known in the art.

Another embodiment relates to the polypeptides comprising the targeting domains described herein (e.g., FIGS. 7A-7E) coupled to a moiety, such as a therapeutic moiety or a dtection moiety. The moiety may be any molecule. Examples of therapeutic moieties include, but are not limited to, ricin, radioisotopes, or clotting or thrombolytic factors. Examples of a detection moiety include, but are not limited to, radioisotopes, dyes, pigments or fluorescent molecules such as luciferase, fluroscein or commercially available fluorescent molecules from quantum.com. The polypeptide may be coupled to the radiologic or imaging molecule by methods known in the art and used to target delivery of the therapeutic or detection moiety to the liver.

Screening Methods

The methods of this invention can screen for a candidate agent that blocks, suppresses or reduces (including significantly) the binding of the targeting domains. Exemplary types of agents that may be screened for ability to inhibit one or more of the the targeting domains described herein include, but are not limited to, antibodies, an anti-sense molecule directed to one or more polynucleotide sequences encoding the targeting domain, an NGF inhibitory compound, a structural analog, a dominant-negative mutation, immunoadhesin, small molecules having a molecular weight of 100 to 20,000 daltons, 500 to 15,000 daltons, or 1000 to 10,000 daltons. Libraries of small molecules are commercially available.

In many situations, different primary tumors metastasize to different organs. Another embodiment of the present invention is directed to libraries of particular primary tumors made, and to the methods disclosed herein that allow for the identification of genes specific for the site of each secondary metastasis. Conversely, since primary tumors of specific organs appear to express specific homing genes RT-PCR analysis of blood samples will allow the identification of such expression before clinical symptoms of the primary tumor present themselves. Thus the present method may allow the diagnosis of subclinical tumor genesis.

Methods of Treatment

A further aspect of the invention comprises methods of treating metastasis in a subject in need of such treatment. In some embodiments the method comprises administering to a subject in need of such treatment a targeting domain linked to a therapeutic agent in an amount effective to treat the metastasis, or an effective amount of a composition that inhibits the metastasis (e.g., collection of phage or phage expression products identified by the method herein; a targeting domain linked to a therapeutic agent and/or an antibody directed against a polypeptide comprising a targeting domain).

Yet another aspect of the invention relates to kits and compositions comprising the polynucleotides, polypeptides, antibodies or couple moieties described herein.

Methods of Inhibiting Gene Expression

The identification of genes that allow primary tumors to specifically target distant organs as sites of secondary metastasis provides new therapeutic methods of treatment. For example, the ability of tumor cells to induce transcription of an identified gene may be altered. Methods for down regulating genes are well known. It has been shown that antisense RNA introduced into a cell will bind to a complementary mRNA and thus inhibit the translation of that molecule. In a similar manner, antisense single stranded cDNA may be introduced into a cell with the same result. Further, co-suppression of genes by homologous transgenes may be effected because the ectopically integrated sequences impair the expression of the endogenous genes (Cogoni et al. Antonie van Leeuwenhoek, 1994; 65(3):205-9), and may also result in the transcription of antisense RNA (Hamada, W. and Spanu, PD; Mol. Gen. Genet 1998). Methods of using short interfering RNA (RNAi) to specifically inhibit gene expression in eukaryotic cells have recently been described. See Tuschl et al., Nature 411:494-498 (2001). In all of the above methods, transfection of cells can be effected using adeno-viral or other viral vectors In addition, stable triple-helical structures can be formed by bonding of oligodeoxyribonucleotides (ODNs) to polypurine tracts of double stranded DNA. (See, for example, Rininsland, Proc. Nat'l Acad. Sci. USA 94:5854-5859 (1997). Triplex formation can inhibit DNA replication by inhibition of transcription of elongation and is a very stable molecule.

Methods to Inhibit the Activity of Specific Proteins

While the present invention can be used to identify genes responsible for the homing and targeting of secondary tumors, the invention also recognized that it will allow the identification of the protein responsible for these phenomena. Thus, it is conceived that the present invention, by identifying that protein, will allow means of affecting gene products at the secondary metastatic site. Specifically, the site of metastasis may be targeted due to a surface protein found in the vascular walls of the endothelium at that site. It will then be possible to affect the expression of that gene down regulating it such that the metastatic tumor cells are not able to enter the endothelium and consequently will be unable to promote secondary tumor growth.

When a specific protein has been implicated in the metastatic ability of primary tumor cells its activity can be altered by several methods. First, specific antibodies may be used to bind the target protein thereby blocking its ability to attract secondary metastasis. In addition, antibodies against the homing protein may be used with a similar result. Such antibodies may be used to bind the protein thereby blocking its activity. Specific antibodies may be obtained though the use of conventional hybridoma technology or may be isolated from libraries commercially available from Dyax (Cambridge, Mass.), MorphoSys (Martinsried, Germany), Biosite (San Diego, Calif.) and Cambridge Antibody Technology (Cambridge, UK). In addition, identified proteins may act as cellular receptors. Identification of such receptors will allow the design of specific ligand antagonists which may affect the metastasis by either 1) binding to the receptor on the metastasizing tumor cell or 2) binding to the target of the metastatic cell in the vasculature at the site of the secondary tumor.

In addition, identification of metastatic proteins also allow for the design of drugs to specifically target both the primary tumor and the secondary tumor. For example, a protein on the surface of a tumor cell that allows it to home-in at a site of secondary metastasis will also allow the design of drugs that bind to, that protein at the site of the primary tumor, as well as, to tumor cells which are embolized in the blood. Similarly, identification of such proteins will allow the design of a drug or agent having an epitope similar to the identified gene product allowing the drug to home-in at the site of the metastases. Thus specific targeting of the primary and secondary tumors may be effected.

In addition, since the invention described herein allows for the identification of genes responsible for metastatic potential of primary tumors, another embodiment of the invention is directed to kits containing primers specific for those genes. Because metastatic tumor cells travel in the blood stream, use of such kits will only necessitate the drawing of blood from a patient and the use of PCR to perform RT-PCR to identify clinically the presence of a tumor, as well as, its metastatic potential.

The following examples illustrate embodiments of the invention, but should not be viewed as limiting the scope of the invention.

EXAMPLES

Example 1

In Vivo Phage Display Identification of Metastatic Cancer Genes

Materials and Methods

Tumor cell lines: Colon cancer cell line (LS174T; American tissue culture collection, ATCC, Rockville, Md.), Melanoma cell line (1205LU; a gift from M. Heerlyn, Wistar Institute, Philadelphia).

Animal: Athymic nude mice were used for the in vivo selection studies.

Generation of cDNA phase libraries: cDNA libraries of the cancer cell lines LS174T and 1205LU were constructed by using the OrientExpress directional random primer strategy (Novagen, Inc.; Darmstadt, DRG). The cDNA were then inserted into a T7Select vector using T7Select 1-1 (up to 1200 amino acids and approximately 1 copy/phage). The cDNA was inserted into the gene of capsid protein 10 and the fusion protein expressed on the surface of the phage capsid (FIG. 1). Using 300 nucleotides as the minimum size of cDNA to be inserted into each phage a library having a diversity of 1-4× $10^6$ was obtained. Once the vectors, which contain the inserts from the cDNA library, were prepared they were packaged into the T-7 phage and amplified in *E. coli* strain BL21 in preparation for biopanning.

Figure 2A:
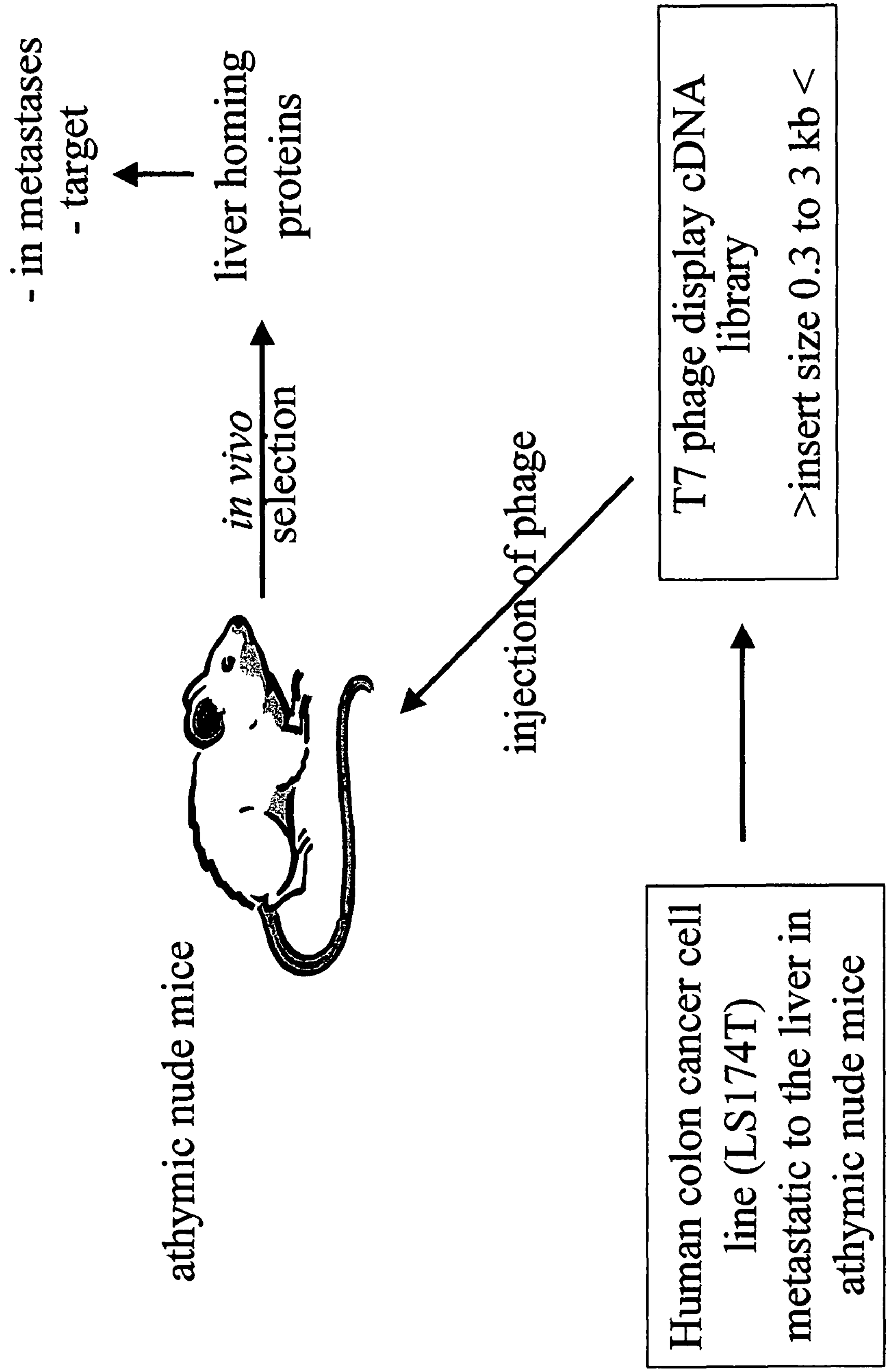
FIG. 2: (A and B) is a schematic representation of the experimental protocol. Mice were injected with the LS174T cDNA expression library over three successive rounds of biopanning using the liver-retained clones. (C) Phage titers after each round of biopanning are illustrated. Corresponding PCR gels created using T7 Up and Down arms as primers reveal band clarification after the second and third rounds of biopanning. (D) Organ distribution of injected phage clones after the fourth round of biopanning is illustrated.
Figure 2B:
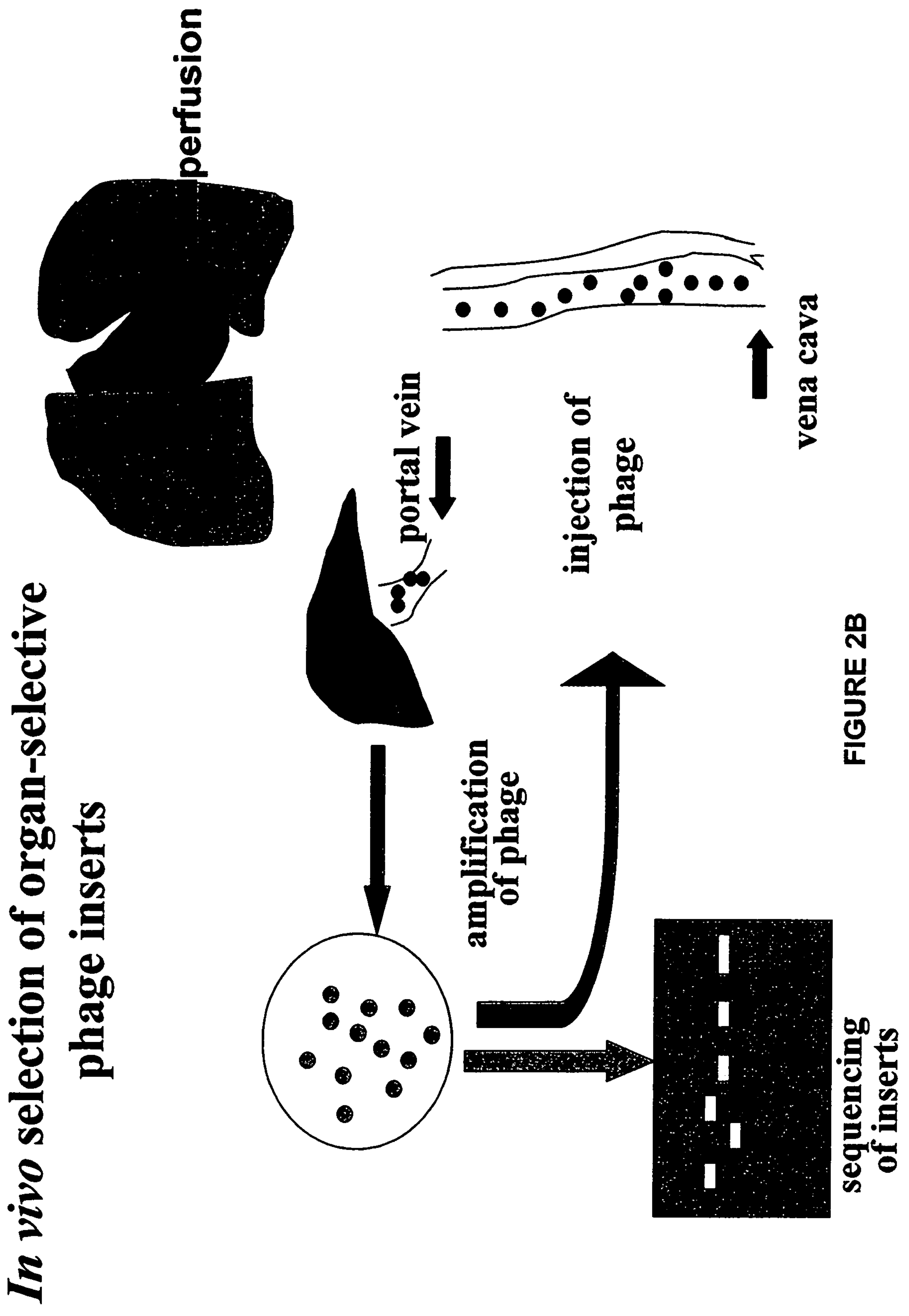

In vivo phage display selection: 100 μl ($10^8$) of stock phage library was intravenously injected into mice (inferior vena cava for LS174T and portal vein for 1205LU) (FIGS. 2A and B). After a circulation time of 5 minutes mice were perfused via the heart and through the inferior vena cava until the perfusate was clear of blood. Liver, lung, kidney and brain were extracted and stored at −80 degrees centigrade. The organ of metastasis (lung or liver) was used to measure the phage titer which was then amplified in *E. coli* in preparation for the subsequent round of biopanning. A total of three to four rounds of biopanning were conducted. The organ-selected library obtained on completion, was used to randomly select plaques for sequencing. Individual clones selected from the target organ, were isolated, amplified and intravenously injected into mice to determine their degree of organ selectivity.

Figure 2C:
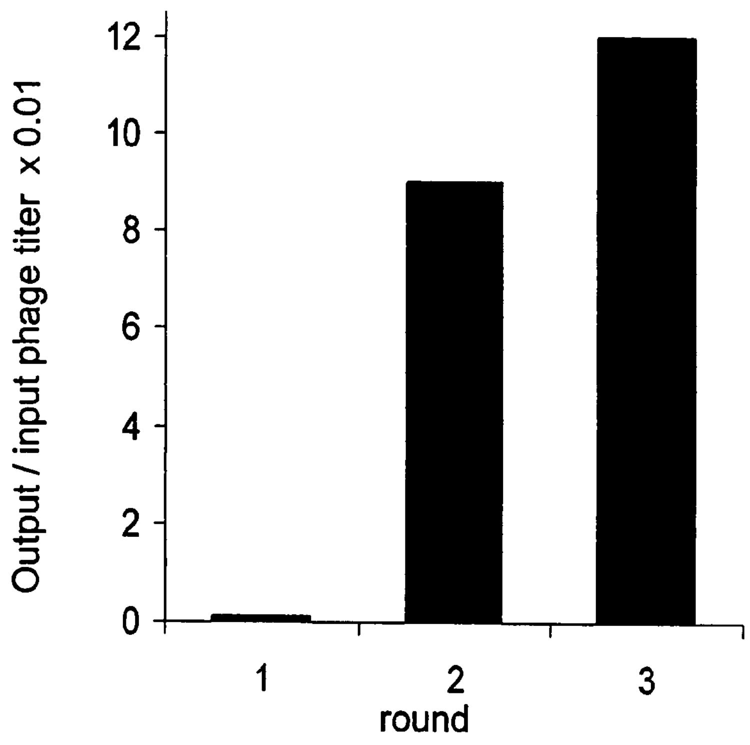
Figure 2D:
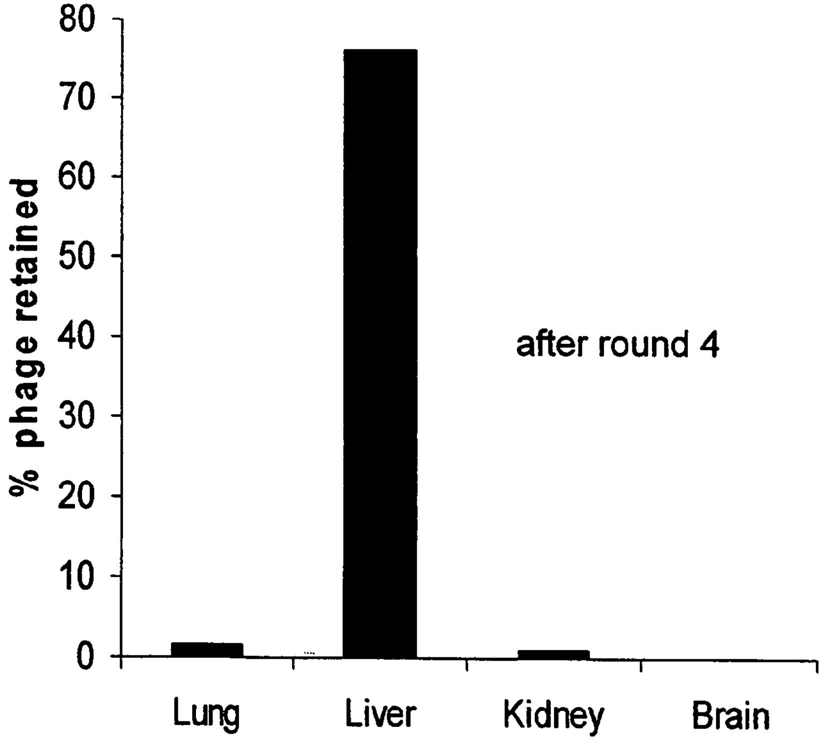

FIG. 2C illustrates the rise in phage titer measured as a percent of phage injected, and quantified from the liver. After the 1st round of biopanning, phage titer retained in the liver was only 0.03% and this rose by almost three logarithms (orders of magnitude) by the third round. By the fourth round of biopanning (FIG. 2D), 97% of the total number of retained phage from the third round, were retained in the liver, compared to just over 2% in the lungs and well under 1% in both the kidneys and brain (FIG. 2D). Alternatively, 76% of the total number of phage injected from the third round, were retained in the liver, indicating that after four rounds of biopanning, clones were selected which predominantly favored the liver.

Identification of Clones: The clones selected by 4 rounds of biopanning were plated. Sixty plaques were selected, amplified by PCR using primers from T7 and the nucleotide sequence determined. The number of clones sequenced depended upon the degeneracy of the library with respect to each clone. The sequences were then analyzed and the identity of the gene obtained by using the BLAST (n) program. Translated sequences started at the 5' EcoR1 site (GAAT TC) at the 5' junction between the T-7 select vector and the tumor cell gene. Any one of the three frames in which translation occurred was used as the authentic frame for translation. In the case of known genes, all three frames were run through the BLAST (p) program to determine the correct frame for translation. For unknown genes, only frame translations, which were twenty amino acids or longer were used. The obtained amino acid sequences from various clones were grouped and analyzed by the CLUSTALW program (for multiple sequence alignment) in search of regions of homology among multiple clones.

Twenty five distinct clones were identified. Of the twenty five identified, seven were of unknown identity, fifteen were known to be either nuclear or cytoplasmic proteins, and one was associated with the cell membrane. Very surprisingly, none of the proteins identified were known to traverse the cell membrane. Of the twenty five different clones, LS42 was the most abundant being repeated seventeen times. A BLASTp search of the 151 amino acid insert shows that this peptide completely matched PA28 alpha subunit or IGUP 1-5111 from position 99 to 248. In the full length protein the first twenty four amino acids are indicated as the molecule's signal peptide allowing for secretion from the cytoplasm. Other than exhibiting 29% identity with β myosin heavy chain, this protein does not appear to be a member of a known family of proteins. However, it bears the cell adhesion motif RGD tripeptide. These results are both surprising and unexpected as a role for cell adhesion by PA28alpha subunit has never been reported.

Immunohistochemistry

To demonstrate that the retention of clones in the liver was not due to non-specific trapping but to direct binding to vascular cells, liver sections were probed with a T7 tag antibody and detected phage by immunohistochemistry. Localization of bacteriophage injected into mice was determined by immunohistochemistry analysis of brain, lung, liver and kidney tissue sections. After mice had been injected with bacterophage and subsequently perfused, brain, lung, kidney and liver were removed and placed in 10% formaldehyde for 1-2 hours. Organs were then placed in 70% ethyl alcohol for at least two hours. Organs were embedded and sectioned and immunohistochemistry of tissue sections on glass slides was carried out. Briefly, embedding medium and formaldehyde were removed by pre-heating slides overnight at 550 C, followed by multiple treatments with xylene and ethanol. Sections were washed, blocked with 10% horse serum and after several more washes with phosphate buffered saline, (PBS), incubated with the primary antibody overnight. The following day sections were washed with PBS after which the biotinylated second antibody was added. Positive reactions were detected with avidin-biotin complex followed by incubation with DAB solution. Positive staining appeared as dark brown.

Northern Blot Analysis

Total RNA from cell lines was isolated with the RNA STAT-60 method (Tel-test, Friendswood, Tex.). RNA was separated and blotted as previously described (Fang et al., JBC, 1992, 267:25889-97). Blots were hybridized, washed and autoradiographed for 48 hrs with cDNA complementary to the gene which encodes for the 151 amino acid expression product for PA28a subunit. Glyceraldehyde-3-phosphate dehydrogenase (GAPDH) was used as a loading control.

In Situ Hybridization

To demonstrate that clones thus far identified in the mouse are significant in humans, phage inserts were used to prepare probes which were then used to probe human tissue arrays of both normal and cancer tissues. These tissue samples included breast, prostate, colon, brain and lymphatic system and both primary and metastatic tissue. In situ hybridization's were carried out as previously described (Stiletto et al., 2000). Briefly, deparaffinized sections of fomalin-fixed tissues were treated at 37° C. for 10 minutes with proteinase K and then washed twice with SSC. Slides were incubated overnight with respective oligonucleotides, in hybridization solution (50% formamide, 4×SSC, 1× Denhardt's solution, 5 mg/ml heat denatured salmon sperm DNA, 2.5 mg/ml yeast tRNA, 10% dextran sulfate). Slides were washed with 2×SSC for 30 minutes at room temperature, with 2×SSC/formamide at 50° C. and with 1×SSC at room temperature for five minutes. Anti-digoxigenin-alkaline phosphatase conjugate was used for immunological detection of bound probes. In the breast cancer tissues, the results showed that the gene was strongly expressed in three cases, medium expression in four cases and little or no expression in five cases. Out of the six clones tested three, PA28a, Epsilon tubule chain, and CAT-292E10, showed positive staining in both the primary and metastatic tumor tissue, leaving the surrounding non cancerous tissue unstained.

Organ Homing by Individual Clones

Figure 3A:
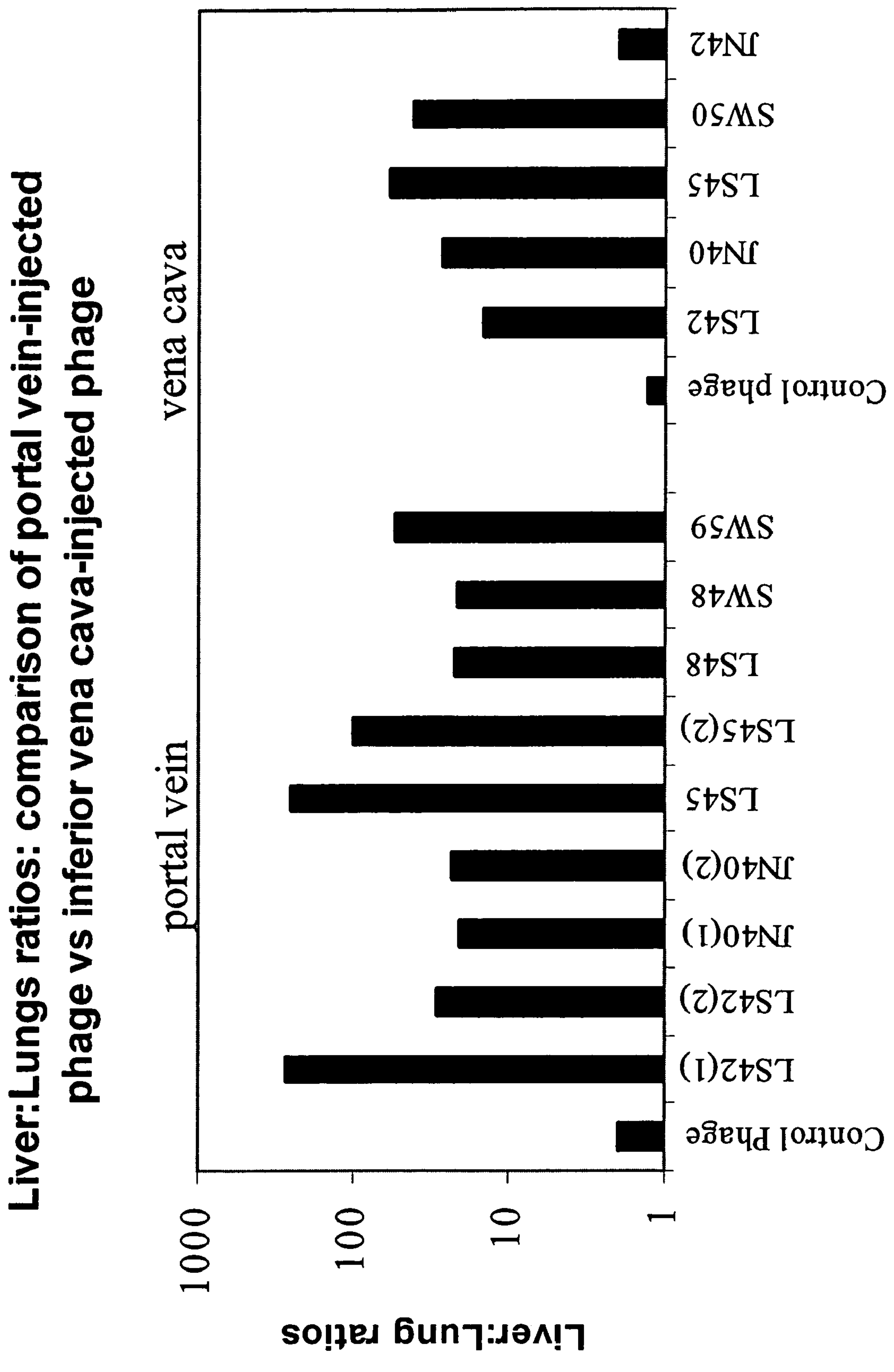
FIG. 3: (A) shows the degree of liver selectivity by individual phage clones injected into immunodeficient non-tumor bearing mice. Comparison is made between the portal vein and inferior vena cava. Titers of individual clones represented as a proportion of the phage numbers from kidneys of the respective animals are shown. (B) Using the two vascular beds with the largest volume, numbers for lung and liver binding (RCF of 1205LU) in each animal are presented together. Each bar represents the mean of three platings.

After identification of the first twenty five clones from the liver-selective library, it was determine whether individual clones were capable of favoring the liver after being intravenously injected into mice. The nine most abundant clones were individually amplified and separately injected into no-tumor bearing mice (FIG. 4). The nucleic acid sequences for the nine clones are provided in FIGS. 6A-C. Translations of the three reading frames for all nine clones is provided in FIGS. 7A-E. To minimize the possibility that clones were retained in the liver because of direct blood flow from portal vein injections, a selection of clones were also injected, in separate mice, through the inferior vena cava, and organ distribution of retained phage estimated. FIG. 2D illustrates the organ distribution of phage injected into mice via the inferior vena cava or portal vein. To standardize the phage numbers among different experiments, phage titers were represented as a proportion of the kidney titers within each experiment. Phage titers in the kidneys were selected for comparison since they were not in the direct circulatory pathway of phage injected either via the inferior vena cava or portal vein. This new number was then used to calculate the liver to lung ratio which was finally used as a measure of liver selectivity. A ratio of one indicates that the clone was distributed equally between the lungs and liver. Injection of the control, wild type T7 phage via the inferior vena cava resulted in a liver to lung ratio of just over one. A slight preference for the liver (two fold) was seen when the route of injection was the portal vein (FIG. 3A).

Figure 5:
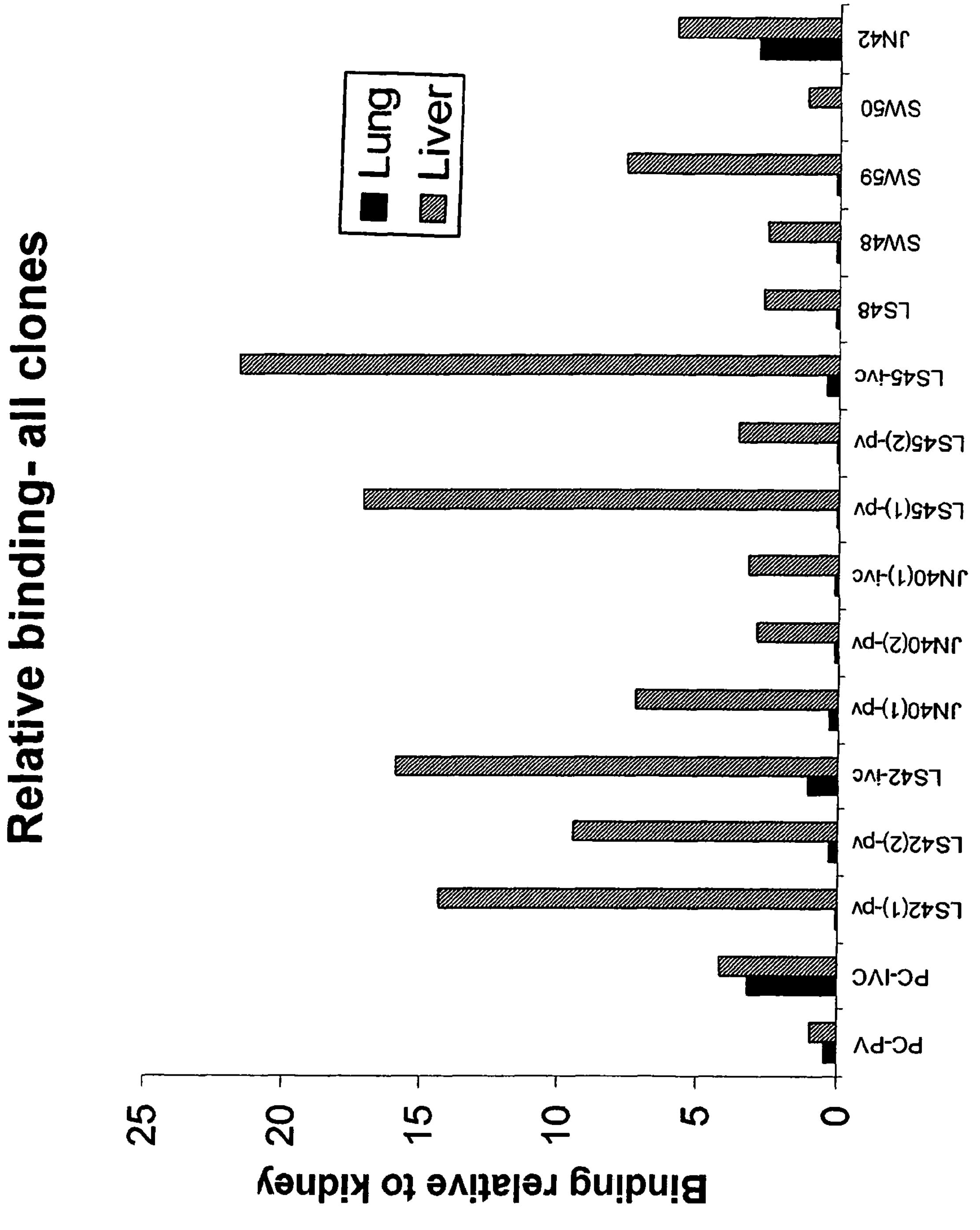
FIG. 5: shows the relative binding of all clones to lung and liver as compared to kidney.

Despite greater liver to lung ratios when the route of delivery was the portal vein as compared to the inferior vena cava, there was a clear preference for the liver in the clones tested (at least fourteen fold), in comparison to the numbers seen with the control, empty T7 phage (FIG. 5). While some of the repeat experiments for individual clones showed variable numbers (e.g. 29 fold and 270 fold for PA28a), all ratios were well above those seen for control phage. Thus, the clones selected for intravenous injection are mostly liver-selective. As further confirmation of the selectivity of these clones, the only clone injected individually whose sequence was outside the open reading frame, JN42, displayed a very weak level of selectivity (two fold), comparable to that of the control phage.

Figure 3B:
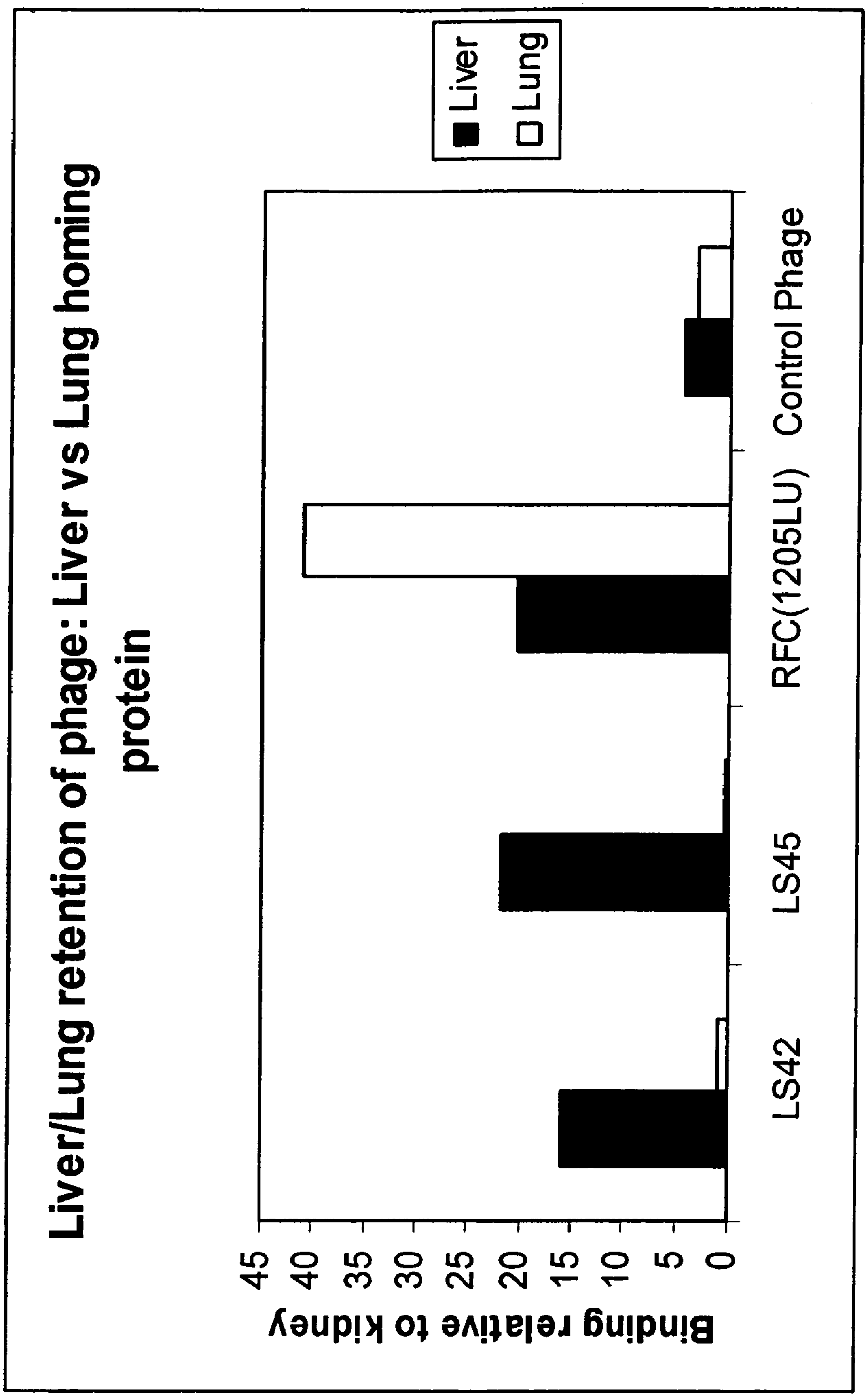

To demonstrate that the method described herein is generally applicable to all possible metastatic tissues, a cell line known to metastasize to organs besides the liver was tested. One of the tumor cell lines used was the human melanoma cell line 1205LU which predominantly metastasizes to the lungs. Using the same principal as that previously described for LS174T, a cDNA library was generated from 1205LU which was then spliced into the T7 phage. After biopanning this library in mice, individual clones were tested for their ability to preferentially home to the lungs (FIG. 3B). In spite of skepticism in the literature about being able to show selection in the lungs due to their high perfusion, a preference of the RFC2 clone for the lugs over the liver by 2.9 fold was shown (see Pasqualini and Ruoslahti Nature 38:1996, 364-366).

Identification of genes that predict and potentially drive metastasis in patients with gastrointestinal carcinoma can be a key concern for diagnostics and therapy.

Patients with different cancers as well as a secreted fibroblast growth factor binding protein (FGF-BP) that is upregulated early in the progression of colon cancer, i.e. dysplasia. We report the mRNA expression of five of the novel metastasis genes from phage display as well as PTN and FGFBP using a series of 39 tissue microarrays representing cancers of the pancreas (n=106), ampulla (n=54), bile duct (n=40), colon (n=37) and liver metastases from colon cancers (n=35). Each of these tumors was represented by several cores on the arrays (mean 4.8±2.6) and 708 cores of 22 different reference tissues were used as controls. Staining for mRNA was performed by in situ hybridization (ISH) with digoxigenin-labeled antisense mRNA probes.

Corresponding controls were performed with sense probes. Staining was evaluated without prior knowledge of the clinical data. Each core was classified according to staining intensity and frequency and tumor cases were classified by percentage of positively staining cancer cells into 6 groups from negative to highly positive.

Results show a distinct frequency and intensity of gene expression in most of the primary lesions (56.2%-92.2%) and very high expression in the liver metastases (69.09-100%). Expression of all of the genes was low in the pancreas non-adeno-carcinoma (25.8-27.3%) and in the according non-neoplastic reference tissues (0%-25%).

A subsequent comparison of patient cases with and without known metastasis showed highly significant increases in expression levels and frequency of the phage-display derived metastasis genes and of PTN for the cases with metastasis (FIG. 8). Tumors with known metastasis typically showed >75% positive tumor cells. Tumors with low or now expression (<25%) were typically without metastasis (all p-values <0.05). No significant correlations were found for FGF-BP. We conclude that genes discovered by phage display and PTN can serve to distinguish amongst GI cancers with different stage and outcome.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

The invention claimed is:

1. A method of identifying a nucleic acid encoding a targeting domain associated with liver metastasis, the method comprising:

(a) injecting into a subject a library of phage displaying a collection of polypeptides expressed from nucleic acids that are greater than 100 nucleotides in length and that are derived from a eukaryotic cell, wherein each polypeptide is expressed from the library of phage at a copy number of about 0.1 copy to about 1 copy per phage;

(b) collecting from the subject's liver phage that, based on the displayed polypeptide, target to and are retained by the liver;

(c) repeating steps (a) and (b) with phage collected in (b) for one or more cycles; and (d) identifying from phage collected in (b) one or more nucleic acids encoding a targeting domain that is associated with liver metastasis, wherein, if the phage does not display a polypeptide, it exhibits low relative retention by the liver.

2. The method of claim 1, wherein the eukaryotic cell is a tumor cell.

3. The method of claim 2, wherein the tumor cell is a primary tumor cell selected from the group consisting of cells of lung, stomach, colon, rectum, prostate, pancreas, liver, leukemia, breast, uterus, ovary, melanoma, urinary tract, bladder, cervix, lymph, brain, and nervous system.

4. The method of claim 1, wherein the phage contain recombinant nucleic acid fragments of greater than 300 nucleotides in length.

5. The method of claim 1, wherein the subject is perfused until the perfusate is clear of blood prior to collection of phage.

6. The method of claim 5, wherein perfusion is performed with an isotonic salt solution with or without proteins.

7. The method of claim 6, wherein perfusion is carried out for greater than the blood volume of the subject.

8. The method of claim 1, wherein the phage host strain is T7.

9. A method of identifying a nucleic acid encoding a targeting domain associated with lung metastasis, the method comprising:

(a) injecting into a subject a library of phage displaying a collection of polypeptides expressed from nucleic acids that are greater than 100 nucleotides in length and that are derived from a eukaryotic cell, wherein each polypeptide is expressed from the library of phage at a copy number of about 0.1 copy to about 1 copy per phage;

(b) collecting from the subject's lung phage that, based on the displayed polypeptide, target to and are retained by the lung;

(c) repeating steps (a) and (b) with phage collected in (b) for one or more cycles; and (d) identifying from phage collected in (b) one or more nucleic acids encoding a targeting domain that is associated with lung metastasis, wherein, if the phage does not display a polypeptide, it exhibits low relative retention by the lung.

10. The method of claim 9, wherein the eukaryotic cell is a tumor cell.

11. The method of claim 10, wherein the tumor cell is a primary tumor cell selected from the group consisting of cells of lung, stomach, colon, rectum, prostate, pancreas, liver, leukemia, breast, uterus, ovary, melanoma, urinary tract, bladder, cervix, lymph, brain, and nervous system.

12. The method of claim 9, wherein the phage contain recombinant nucleic acid fragments of greater than 300 nucleotides in length.

13. The method of claim 9, wherein the subject is perfused until the perfusate is clear of blood prior to collection of phage.

14. The method of claim 13, wherein perfusion is performed with an isotonic salt solution with or without proteins.

15. The method of claim 14, wherein perfusion is carried out for greater than the blood volume of the subject.

16. A method of identifying a nucleic acid encoding a targeting domain associated with metastasis, the method comprising:

(a) injecting into a subject a library of phage displaying a collection of polypeptides expressed from nucleic acids that are greater than 100 nucleotides in length and that are derived from a eukaryotic cell, wherein each polypeptide is expressed from the library of phage at a copy number of about 0.1 copy to about 1 copy per phage;

(b) perfusing the subject until the perfusate is clear of blood, wherein perfusion is performed with an isotonic salt solution with or without proteins;

(c) collecting phage which, based on the displayed polypeptide, target to and are retained by an organ or tissue;

(d) repeating steps (a)-(c) with phage collected in (c) for one or more cycles; and (e) identifying from phage collected in (c) one or more nucleic acids encoding a targeting domain that is associated with metastasis, wherein, if the phage does not display a polypeptide, it exhibits low relative retention by the organ or tissue.

17. The method of claim 16, wherein perfusion is carried out for greater than the blood volume of the subject.

18. A collection of phage expressing a cDNA library generated from the cell line LS174T or 1205LU, wherein cDNA that is greater than 100 nucleotides in length and that comprises a targeting domain that is associated with liver metastasis is expressed from the library of phage at a copy number of about 0.1 copy to about 1 copy per phage, wherein, if the phage does not display a polypeptide, it exhibits low relative retention by the liver.

19. The collection of phage of claim 18, wherein the phage host strain is T7.

20. A collection of phage expressing a cDNA library generated from the cell line LS174T or 1205LU, wherein cDNA that is greater than 100 nucleotides in length and that comprises a targeting domain that is associated with lung metastasis is expressed from the library of phage at a copy number of about 0.1 copy to about 1 copy per phage, wherein, if the phage does not display a polypeptide, it exhibits low relative retention by the lung.

21. An isolated polynucleotide that comprises (a) a nucleic acid selected from the group consisting of SEQ ID NOs: 1-6 and 9 or (b) a nucleic acid that encodes a targeting domain that is associated with metastasis and is a full length complement of a nucleic acid selected from the group consisting of SEQ ID NOs: 1-9 or a variant due to the degeneracy of the genetic code of a nucleic acid selected from the group consisting of SEQ ID NOs: 1-9.

22. A polypeptide encoded by a polynucleotide of claim 21, wherein the polypeptide comprises an amino acid sequence selected from the group consisting of SEQ ID NOs: 10-36.

23. An isolated polynucleotide that encodes a polypeptide comprising a polypeptide sequence selected from the group consisting of SEQ ID NOs: 10-36, wherein the polynucleotide is not SEQ ID NO: 7 or SEQ ID NO: 8, and wherein the polynucleotide encodes a targeting domain that is associated with metastasis.

24. A polypeptide comprising one or more of the polypeptide sequences selected from the group consisting of SEQ ID NOs: 10-29 and 31-36, wherein the one or more polypeptide sequences comprises a targeting domain that is associated with metastasis.

25. The polypeptide of claim 24 that is coupled to a moiety.

26. The polypeptide of claim 25, wherein the moiety is a therapeutic moiety or a detection moiety.

27. The polypeptide of claim 26, wherein the therapeutic moiety is a radioactive isotope or a cytotoxic agent.

28. The polypeptide of claim 26, wherein the detection moiety is a radioactive isotope, a pigment or a dye.

29. A microarray comprising one or more of the polynucleotides of claim 21.

30. A microarray comprising one or more of the polypeptides of claim 24.

31. A kit comprising one or more of the polynucleotides of claim 21.

32. A kit comprising one or more of the polypeptides of claim 24.

33. An isolated polynucleotide of SEQ ID NO: 7 that encodes a targeting domain that is associated with metastasis.

34. An isolated polynucleotide of SEQ ID NO: 8 that encodes a targeting domain that is associated with metastasis.

35. A polypeptide of SEQ ID NO: 30 comprising a targeting domain that is associated with metastasis.

* * * * *